United States Patent
Galen

(10) Patent No.: US 7,459,161 B2
(45) Date of Patent: Dec. 2, 2008

(54) METHODS FOR ELICITING AN IMMUNE RESPONSE USING CYTOLYSIN AND HEMOLYSIN FUSION PROTEINS

(75) Inventor: James E. Galen, Owings Mills, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 401 days.

(21) Appl. No.: 11/298,526

(22) Filed: Dec. 12, 2005

(65) Prior Publication Data

US 2006/0147461 A1    Jul. 6, 2006

Related U.S. Application Data

(62) Division of application No. 09/993,292, filed on Nov. 23, 2001, now Pat. No. 7,056,700.

(60) Provisional application No. 60/252,516, filed on Nov. 22, 2000.

(51) Int. Cl.
     *A61K 39/02*      (2006.01)
     *A01N 63/00*      (2006.01)

(52) U.S. Cl. .................. 424/200.1; 424/93.2; 424/93.4; 435/71.2; 435/252.3

(58) Field of Classification Search ........................ None
See application file for complete search history.

(56) References Cited

U.S. PATENT DOCUMENTS

| | | |
|---|---|---|
| 4,235,877 A | 11/1980 | Fullerton |
| 4,355,117 A | 10/1982 | Antrim et al. |
| 4,372,945 A | 2/1983 | Likhite |
| 4,474,757 A | 10/1984 | Arnon et al. |
| 4,665,027 A | 5/1987 | Dale et al. |
| 4,910,139 A | 3/1990 | Chang et al. |
| 5,387,744 A | 2/1995 | Curtiss, III et al. |
| 5,512,480 A | 4/1996 | Sandstrom et al. |
| 5,525,504 A | 6/1996 | Goebel et al. |
| 5,585,266 A | 12/1996 | Plitt et al. |
| 5,635,368 A | 6/1997 | Lommi et al. |
| 5,731,151 A | 3/1998 | King et al. |
| 6,413,768 B1 | 7/2002 | Galen |

FOREIGN PATENT DOCUMENTS

| | | |
|---|---|---|
| WO | WO 94 28137 | 12/1994 |
| WO | WO 01 75067 | 10/2001 |

OTHER PUBLICATIONS

Ikonomidis et al, *J. Exp. Med.*, 180:2209-2218 (1994).
Gerhold et al., *BioEssays*, 18(12):973-981 (1996).
Wells et al, *J. of Leukocyte Biology*, 61(5):545-550 (1997).
Russell et al, *J. of Mol. Biol.*, 244:332-350 (1994).
Attwood, *Science*, 290:471-473 (2000).
Atkins et al, *J. Biol. Chem.*, 275:41150-41155 (2000).
Bramucci et al., *Appl. Environ. Microbial.*, 62:3948-3953 (1996).
Corchero et al, *Biotechnol. Bioeng.*, 58:625-632 (1998).
Cserjan-Puschmann et al, *Appl. Microbiol. Biotechnol.*, 53:43-50 (1999).
del Castillo et al, *Mol. Microbiol.*, 25:107-115 (1997).
Galen et al, *Trends of Microbiology*, 9:372-376 (2001).
Hess et al, *Proc. Natl. Acad. Sci. USA*, 93:1458-1463 (1996).
Ludwig et al, *Mol. Microbiol.*, 31:557-567 (1999).
Wallace et al, *Cell*, 100:265-276 (2000).
Tzschaschel et al, *Nature Biotechnology*, 14:765-769 (1996).
Gentschev et al, *Behring Inst. Mitteilungen*, 98:103-113 (1997).
Ryan et al, *Infect. and Immunity*, 65(7):2941-2949 (1997).
Hahn et al, *FEMS Immunology and Medical Microbiology*, 20(2):111-119 (1998).
Su et al, *Microbial Pathogenesis*, 13:465-476 (1992).
Saarilahti et al, *Infection and Immunity*, 57:3663-3665 (1989).
Schodel et al, *Infection and Immunity*, 57:1347-1350 (1989).

*Primary Examiner*—Patricia A Duffy

(57) ABSTRACT

The disclosure below provides a protein export system for efficiently producing recombinant protein from a host cell. In a preferred embodiment, the protein export system utilizes protein export machinery endogenous to the host bacterium into which the protein export system vector is introduced.

7 Claims, 4 Drawing Sheets

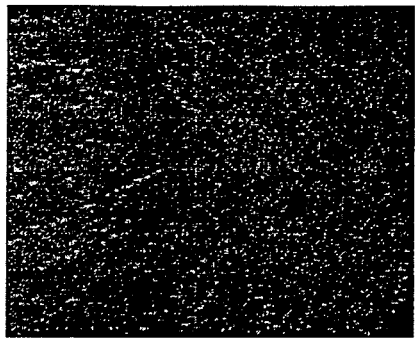 
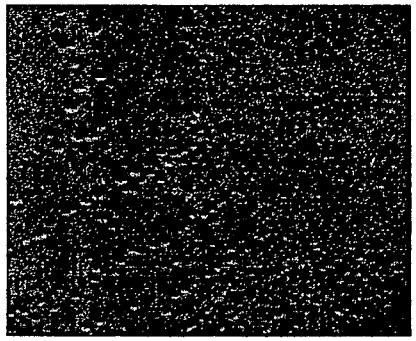 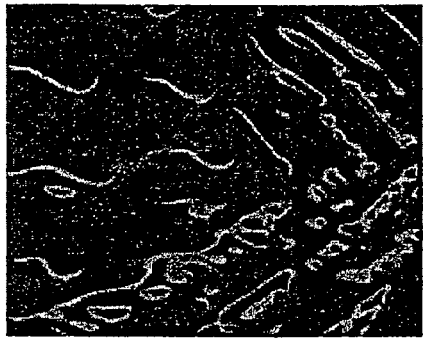
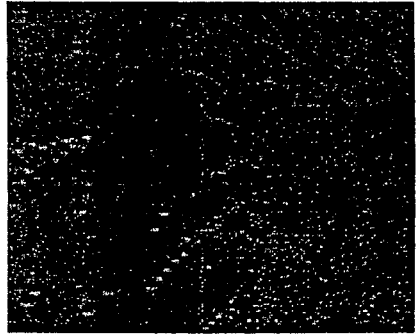 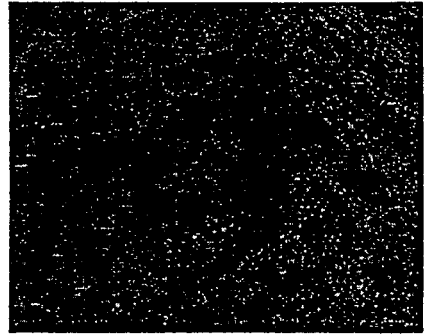
FIG. 2

SEQUENCE LISTING

```
<160> NUMBER OF SEQ ID NOS: 25

<210> SEQ ID NO 1
<211> LENGTH: 6271
<212> TYPE: DNA
<213> ORGANISM: Artificial Sequence
<220> FEATURE:
<223> OTHER INFORMATION: pSEC84 Expression Plasmid

<400> SEQUENCE: 1
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300 tttttgaaaca tctatagcga taaatgaaac atcttaaaag ttttagtatc atattcgtgt     360
tggattattc tgcatttttg gggagaatgg acttgccgac tgattaatga gggttaatca     420
gtatgcagtg gcataaaaaa gcaaataaag gcatataaca gatcgatctt aaacatccac     480
```

```
aggaggatgg gatccaaaat aaggaggaaa aaaaaatgac tagtattttt gcagaacaaa      540
ctgtagaggt agttaaaagc gcgatcgaaa ccgcagatgg ggcattagat ctttataaca      600
aatacctcga ccaggtcatc ccctggaaga cctttgatga aaccataaaa gagttaagcc      660
gttttaaaca ggagtactcg caggaagctt ctgttttagt tggtgatatt aaagttttgc      720
ttatggacag ccaggacaag tattttgaag cgacacaaac tgtttatgaa tggtgtggtg      780
tcgtgacgca attactctca gcgtatattt tactatttga tgaatataat gagaaaaaag      840
catcagccca gaaagacatt ctcattagga tattagatga tggtgtcaag aaactgaatg      900
aagcgcaaaa atctctcctg acaagttcac aaagtttcaa caacgcttcc ggaaaactgc      960
tggcattaga tagccagtta actaatgatt tttcggaaaa aagtagttat ttccagtcac     1020
aggtggatag aattcgtaag gaagcttatg ccggtgctgc agccggcata gtcgccggtc     1080
cgtttggatt aattatttcc tattctattg ctgcgggcgt gattgaaggg aaattgattc     1140
cagaattgaa taacaggcta aaaacagtgc aaaatttctt tactagctta tcagctacag     1200
tgaaacaagc gaataaagat atcgatgcgg caaaattgaa attagccact gaaatagcag     1260
caattgggga gataaaaacg gaaaccgaaa caaccagatt ctacgttgat tatgatgatt     1320
taatgctttc tttattaaaa ggagctgcaa agaaaatgat taacacctgt aatgaatacc     1380
aacaacgtca tggtaagaag acgcttttcg aggttcctga cgtcgctagc tgataaccta     1440
gggccagcaa aaggccagga accgtaaaaa ggccgcgttg ctggcgtttt tccataggct     1500
ccgcccccct gacgagcatc acaaaaatcg acgctcaagt cagaggtggc gaaacccgac     1560
aggactataa agataccagg cgtttccccc tggaagctcc ctcgtgcgct ctcctgttcc     1620
gaccctgccg cttaccggat acctgtccgc ctttctccct tcgggaagcg tggcgctttc     1680
tcatagctca cgctgtaggt atctcagttc ggtgtaggtc gttcgctcca agctgggctg     1740
tgtgcacgaa ccccccgttc agcccgaccg ctgcgcctta tccggtaact atcgtcttga     1800
gtccaacccg gtaagacacg acttatcgcc actggcagca gccactggta acaggattag     1860
cagagcgagg tatgtaggcg gtgctacaga gttcttgaag tggtggccta actacggcta     1920
cactagaagg acagtatttg gtatctgcgc tctgctgaag ccagttacct tcggaaaaag     1980
agttggtagc tcttgatccg gcaaacaaac caccgctggt agcggtggtt ttttgtttg     2040 caagcagcag attacgcgca gaaaaaaagg atctcaagaa gatcctttga tcttttctac     2100
ggggtctgac gctcagtaga tctaaaacac taggcccaag agtttgtaga acgcaaaaa     2160 ggccatccgt caggatggcc ttctgcttaa tttgatgcct ggcagtttat ggcgggcgtc     2220
ctgcccgcca ccctccgggc cgttgcttcg caacgttcaa atccgctccc ggcggatttg     2280
tcctactcag gagagcgttc accgacaaac aacagataaa acgaaaggcc cagtctttcg     2340
actgagcctt tcgttttatt tgatgcctgg cagttcccta ctctcgcatg gggagacccc     2400
acactaccat cggcgctacg gcgtttcact tctgagttcg gcatgggtc aggtgggacc     2460 accgcgctac tgccgccagg caaattctgt tttatcagac cgcttctgcg ttctgattta     2520
atctgtatca ggctgaaaat cttctctcat ccgccaaaac agccaagctg atctggcaa     2580 atcgctgaat attcctttg tctccgacca tcaggcacct gagtcgctgt cttttcgtg     2640 acattcagtt cgctgcgctc acggctctgg cagtgaatgg gggtaaatgg cactacaggc     2700
gccttttatg gattcatgca aggaaactac ccataataca agaaaagccc gtcacgggct     2760
tctcagggcg ttttatggcg gtctgctat gtggtgctat ctgactttt gctgttcagc     2820 agttcctgcc ctctgatttt ccagtctgac cacttcggat tatcccgtga caggtcattc     2880
```

```
agactggcta atgcacccag taaggcagcg gtatcatcaa caggcttacc cgtcttactg    2940
tcaaccggat ctaaaacact agcccaacct ttcatagaag gcggcggtgg aatcgaaatc    3000
tcgtgatggc aggttgggcg tcgcttggtc ggtcatttcg aaccccagag tcccgctcag    3060
aagaactcgt caagaaggcg atagaaggcg atgcgctgcg aatcgggagc ggcgataccg    3120
taaagcacga ggaagcggtc agcccattcg ccgccaagct cttcagcaat atcacgggta    3180
gccaacgcta tgtcctgata gcggtccgcc acacccagcc ggccacagtc gatgaatcca    3240
gaaaagcggc cattttccac catgatattc ggcaagcagg catcgccatg ggtcacgacg    3300
agatcctcgc cgtcgggcat gcgcgccttg agcctggcga acagttcggc tggcgcgagc    3360
ccctgatgct cttcgtccag atcatcctga tcgacaagac cggcttccat ccgagtacgt    3420
gctcgctcga tgcgatgttt cgcttggtgg tcgaatgggc aggtagccgg atcaagcgta    3480
tgcagccgcc gcattgcatc agccatgatg atactttct cggcaggagc aaggtgagat    3540
gacaggagat cctgccccgg cacttcgccc aatagcagcc agtcccttcc cgcttcagtg    3600
acaacgtcga gcacagctgc gcaaggaacg cccgtcgtgg ccagccacga tagccgcgct    3660
gcctcgtcct gcagttcatt cagggcaccg gacaggtcgg tcttgacaaa aagaaccggg    3720
cgcccctgcg ctgacagccg gaacacggcg gcatcagagc agccgattgt ctgttgtgcc    3780
cagtcatagc cgaatagcct ctccacccaa gcggccggag aacctgcgtg caatccatct    3840
tgttcaatca tgcgaaacga tcctcatcct gtctcttgat cagatcttga tccctgcgc    3900 catcagatcc ttggcggcaa gaaagccatc cagtttactt tgcagggctt cccaaccta    3960 ccagagggcg ccccagctgg caattccggt tcgctgctag acaacatcag caaggagaaa    4020
ggggctaccg gcgaaccagc agcccctta taaaggcgct tcagtagtca gaccagcatc    4080
agtcctgaaa aggcgggcct gcgcccgcct ccaggttgct acttaccgga ttcgtaagcc    4140
atgaaagccg ccacctccct gtgtccgtct ctgtaacgaa tctcgcacag cgattttcgt    4200
gtcagataag tgaatatcaa cagtgtgaga cacacgatca acacacacca gacaagggaa    4260
cttcgtggta gtttcatggc cttcttctcc ttgcgcaaag cgcggtaaga ggctatcctg    4320
atgtggacta gacatagga tgcctcgtgg tggttaatga aaattaactt actacggggc    4380
tatcttcttt ctgccacaca acacggcaac aaaccacctt cacgtcatga ggcagaaagc    4440
ctcaagcgcc gggcacatca tagcccatat acctgcacgc tgaccacact cactttccct    4500
gaaaataatc cgctcattca gaccgttcac gggaaatccg tgtgattgtt gccgcatcac    4560
gctgcctccc ggagtttgtc tcgagcactt ttgttacccg ccaaacaaaa cccaaaaaca    4620 acccatacccc aacccaataa aacaccaaaa caagacaaat aatcattgat tgatggttga    4680 aatgggggtaa acttgacaaa caaacccact taaaacccaa aacatacccca aacacacacc    4740 aaaaaaacac cataaggagt tttataaatg ttggtattca ttgatgacgg ttcaacaaac    4800
atcaaactac agtggcagga aagcgacgga acaattaaac agcacattag cccgaacagc    4860
ttcaaacgcg agtgggcagt ctcttttggt gataaaaagg tctttaacta cacactgaac    4920
ggcgaacagt attcatttga tccaatcagc ccggatgctg tagtcacaac caatatcgca    4980
tggcaataca gcgacgttaa tgtcgttgca gtgcatcacg ccttactgac cagtggtctg    5040
ccggtaagcg aagtggatat tgtttgcaca cttcctctga cagagtatta cgacagaaat    5100
aaccaaccca atacggaaaa tattgagcgt aagaagcaa acttccggaa aaaaattaca    5160
ttaaatggcg gggatacatt cacaataaaa gatgtaaaag tcatgcctga atctataccg    5220
gcaggttatg aagttctaca agaactggat gagttagatt ctttattaat tatagatctc    5280
```

```
gggggcacca cattagatat ttctcaggta atggggaaat atcgggat cagtaaaata   5340
tacggagact catctcttgg tgtctctctg gttacatctg cagtaaaaga tgcccttct   5400
cttgcgagaa caaaggaag tagctatctt gctgacgata taatcattca cagaaaagat   5460
aataactatc tgaagcaacg aattaatgat gagaacaaaa tatcaatagt caccgaagca   5520
atgaatgaag cacttcgtaa acttgagcaa cgtgtattaa atacgctcaa tgaattttct   5580
ggttatactc atgttatggt tataggcggt ggcgcagaat taatatgcga tgcagtaaaa   5640
aaacacacac agattcgtga tgaacgtttt ttcaaaacca ataactctca atatgattta   5700
gttaacggta tgtatctcat aggtaattaa tgatggacaa gcgcagaacc attgccttca   5760
aactaaatcc agatgtaaat caaacagata aaattgtttg tgatacactg gacagtatcc   5820
cgcaagggga acgaagccgc cttaaccggg ccgcactgac ggcaggtctg gccttataca   5880
gacaagatcc ccggacccct ttccttttat gtgagctgct gacgaaagaa accacatttt   5940
cagatatcgt gaatatattg agatcgctat ttccaaaaga gatggccgat ttaattctt   6000
caatagtcac tcaatcctct tcacaacaag agcaaaaaag tgatgaagag accaaaaaaa   6060
atgcgatgaa gctaataaat taattcaatt attattgagt tccctttatc cactatcagg   6120
ctggataaag ggaactcaat caagttattt tcttaccagt cattacataa tcgttattat   6180
gaaataatcg tttgcactgt ctctgttatt caggcaattt caataaaggc acttgctcac   6240
gctctgtcat tttctgaaac tcttcatgct g                                 6271
```

<210> SEQ ID NO 2
<211> LENGTH: 305
<212> TYPE: PRT
<213> ORGANISM: Salmonella typhi

<400> SEQUENCE: 2

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile

```
                195                 200                 205
Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Leu Met Leu Ser
            260                 265                 270

Leu Leu Lys Gly Ala Ala Lys Lys Met Ile Asn Thr Cys Asn Glu Tyr
                275                 280                 285

Gln Gln Arg His Gly Lys Lys Thr Leu Phe Glu Val Pro Asp Val Ala
    290                 295                 300

Ser
305

<210> SEQ ID NO 3
<211> LENGTH: 102
<212> TYPE: DNA
<213> ORGANISM: Artificial Sequence
<220> FEATURE:
<223> OTHER INFORMATION: Cloning Primer

<400> SEQUENCE: 3
ggatccaaaa taaggaggaa aaaaaaatga ctagtatttt tgcagaacaa actgtagagg      60
tagttaaaag cgcgatcgaa accgcagatg ggcattaga tc                        102

<210> SEQ ID NO 4
<211> LENGTH: 101
<212> TYPE: DNA
<213> ORGANISM: Artificial Sequence
<220> FEATURE:
<223> OTHER INFORMATION: Cloning Primer

<400> SEQUENCE: 4
cctaggttat cagctagcga cgtcaggaac ctcgaaaagc gtcttcttac catgacgttg      60
ttggtattca ttacaggtgt taatcatttt ctttgcagct c                        101

<210> SEQ ID NO 5
<211> LENGTH: 97
<212> TYPE: DNA
<213> ORGANISM: Artificial Sequence
<220> FEATURE:
<223> OTHER INFORMATION: Cloning Primer

<400> SEQUENCE: 5
cacggtaaga agacgctttt cgaggttcct gacgtcgcta gctgataacc taggtcatgt      60
tagacagctt atcatcgata agctttaatg cggtagt                              97

<210> SEQ ID NO 6
<211> LENGTH: 69
<212> TYPE: DNA
<213> ORGANISM: Artificial Sequence
<220> FEATURE:
<223> OTHER INFORMATION: Cloning Primer

<400> SEQUENCE: 6
agatctacta gtgtcgacgc tagctatcag gtcgaggtgg cccggctcca tgcaccgcga      60
cgcaacgcg                                                             69
```

<210> SEQ ID NO 7
<211> LENGTH: 60
<212> TYPE: DNA
<213> ORGANISM: Artificial Sequence
<220> FEATURE:
<223> OTHER INFORMATION: Cloning Primer

<400> SEQUENCE: 7
actagtcacc cagaaacgct ggtgaaagta aaagatgctg aagatcagtt gggtgcacga      60

<210> SEQ ID NO 8
<211> LENGTH: 101
<212> TYPE: DNA
<213> ORGANISM: Artificial Sequence
<220> FEATURE:
<223> OTHER INFORMATION: Cloning Primer

<400> SEQUENCE: 8
cattaaaggt tatcgatgat aagctgtcaa acatgagcta gcctaggtca ttaccaatgc      60
ttaatcagtg aggcacctat ctcagcgatc tgtctatttc g                        101

<210> SEQ ID NO 9
<211> LENGTH: 101
<212> TYPE: DNA
<213> ORGANISM: Artificial Sequence
<220> FEATURE:
<223> OTHER INFORMATION: Cloning Primer

<400> SEQUENCE: 9
cgaaatagac agatcgctga gataggtgcc tcactgatta agcattggta atgacctagg      60
ctagctcatg tttgacagct tatcatcgat aacctttaat g                        101

<210> SEQ ID NO 10
<211> LENGTH: 71
<212> TYPE: DNA
<213> ORGANISM: Artificial Sequence
<220> FEATURE:
<223> OTHER INFORMATION: Cloning Primer

<400> SEQUENCE: 10
gcgcactagt aaagaaacga accaaaagcc atataaggaa acatacggca tttcccatat      60
tacacgccat g                                                          71

<210> SEQ ID NO 11
<211> LENGTH: 103
<212> TYPE: DNA
<213> ORGANISM: Artificial Sequence
<220> FEATURE:
<223> OTHER INFORMATION: Cloning Primer

<400> SEQUENCE: 11
taaactaccg cattaaagct tatcgatgat aagctgtcaa acatgacccg ggtcactatt      60
tgttaactgt taattgtcct tgttcaagga tgctgtcttt gac                      103

<210> SEQ ID NO 12
<211> LENGTH: 46
<212> TYPE: DNA
<213> ORGANISM: Artificial Sequence
<220> FEATURE:
<223> OTHER INFORMATION: Cloning Primer

<400> SEQUENCE: 12
tcatgtttga cagcttatca tcgataagct ttaatgcggt agttta                    46

```
<210> SEQ ID NO 13
<211> LENGTH: 80
<212> TYPE: DNA
<213> ORGANISM: Artificial Sequence
<220> FEATURE:
<223> OTHER INFORMATION: Cloning Primer

<400> SEQUENCE: 13
gcgcagatct taatcatcca caggaggcgc tagcatgagt aaaggagaag aactttttcac    60 tggagttgtc ccaattcttg                                                 80

<210> SEQ ID NO 14
<211> LENGTH: 110
<212> TYPE: DNA
<213> ORGANISM: Artificial Sequence
<220> FEATURE:
<223> OTHER INFORMATION: Cloning Primer

<400> SEQUENCE: 14
gtgataaact accgcattaa agcttatcga tgataagctg tcaaacatga gcgctctaga    60
actagttcat tatttgtaga gctcatccat gccatgtgta atcccagcag               110

<210> SEQ ID NO 15
<211> LENGTH: 94
<212> TYPE: DNA
<213> ORGANISM: Artificial Sequence
<220> FEATURE:
<223> OTHER INFORMATION: Cloning Primer

<400> SEQUENCE: 15
gcgcactagt aaaaaccttg attgttgggt cgacaacgaa gaagacatcg atgttatcct    60
gaaaaagtct accattctga acttggacat caac                                94

<210> SEQ ID NO 16
<211> LENGTH: 97
<212> TYPE: DNA
<213> ORGANISM: Artificial Sequence
<220> FEATURE:
<223> OTHER INFORMATION: Cloning Primer

<400> SEQUENCE: 16
aactaccgca ttaaagctta tcgatgataa gctgtcaaac atgagctagc ctaggtcatt    60
agtcgttggt ccaaccttca tcggtcggaa cgaagta                             97

<210> SEQ ID NO 17
<211> LENGTH: 30
<212> TYPE: DNA
<213> ORGANISM: Artificial Sequence
<220> FEATURE:
<223> OTHER INFORMATION: Cloning Primer

<400> SEQUENCE: 17
cgatgcggca aaattgaaat tagccactga                                     30

<210> SEQ ID NO 18
<211> LENGTH: 8908
<212> TYPE: DNA
<213> ORGANISM: Artificial Sequence
<220> FEATURE:
<223> OTHER INFORMATION: pSEC84sacB vector

<400> SEQUENCE: 18
gaattctgtg gtagcacaga ataatgaaaa gtgtgtaaag aagggtaaaa aaaaccgaat    60
gcgaggcatc cggttgaaat agggggtaaac agacattcag aaatgaatga cggtaataaa   120
```

```
taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcattttg gggagaatgg acttgccgac tgattaatga gggttaatca     420
gtatgcagtg gcataaaaaa gcaaataaag gcatataaca gatcgatctt aaacatccac    480
aggaggatgg gatccaaaat aaggaggaaa aaaaatgac tagtattttt gcagaacaaa     540
ctgtagaggt agttaaaagc gcgatcgaaa ccgcagatgg ggcattagat ctttataaca    600
aatacctcga ccaggtcatc ccctggaaga cctttgatga aaccataaaa gagttaagcc    660
gttttaaaca ggagtactcg caggaagctt ctgttttagt tggtgatatt aaagttttgc    720
ttatggacag ccaggacaag tattttgaag cgacacaaac tgtttatgaa tggtgtggtg    780
tcgtgacgca attactctca gcgtatattt tactatttga tgaatataat gagaaaaaag    840
catcagccca gaaagacatt ctcattagga tattagatga tggtgtcaag aaactgaatg    900
aagcgcaaaa atctctcctg acaagttcac aaagtttcaa caacgcttcc ggaaaactgc    960
tggcattaga tagccagtta actaatgatt tttcggaaaa aagtagttat ttccagtcac    1020
aggtggatag aattcgtaag gaagcttatg ccggtgctgc agccggcata gtcgccggtc    1080
cgtttggatt aattatttcc tattctattg ctgcgggcgt gattgaaggg aaattgattc    1140
cagaattgaa taacaggcta aaaacagtgc aaaatttctt tactagctta tcagctacag    1200
tgaaacaagc gaataaagat atcgatgcgg caaaattgaa attagccact gaaatagcag    1260
caattgggga gataaaaacg gaaaccgaaa caaccagatt ctacgttgat tatgatgatt    1320
taatgctttc tttattaaaa ggagctgcaa agaaaatgat taacacctgt aatgaatacc    1380
aacaacgtca tggtaagaag acgcttttcg aggttcctga cgtcgctagt aaagaaacga    1440
accaaaagcc atataaggaa acatacggca tttcccatat tacacgccat gatatgctgc    1500
aaatccctga acagcaaaaa aatgaaaaat atcaagttcc tgaattcgat tcgtccacaa    1560
ttaaaaatat ctcttctgca aaaggcctgg acgtttggga cagctggcca ttacaaaacg    1620
ctgacggcac tgtcgcaaac tatcacggct accacatcgt ctttgcatta gccggagatc    1680
ctaaaaatgc ggatgacaca tcgatttaca tgttctatca aaaagtcggc gaaacttcta    1740
ttgacagctg gaaaaacgct ggccgcgtct ttaaagacag cgacaaattc gatgcaaatg    1800
attctatcct aaaagaccaa acacaagaat ggtcaggttc agccacattt acatctgacg    1860
gaaaaatccg tttattctac actgatttct ccggtaaaca ttacggcaaa caaacactga    1920
caactgcaca agttaacgta tcagcatcag acagctcttt gaacatcaac ggtgtagagg    1980
attataaatc aatctttgac ggtgacggaa aaacgtatca aaatgtacag cagttcatcg    2040
atgaaggcaa ctacagctca ggcgacaacc atacgctgag agatcctcac tacgtagaag    2100
ataaaggcca caaatactta gtatttgaag caaacactgg aactgaagat ggctaccaag    2160
gcgaagaatc tttatttaac aaagcatact atggcaaaag cacatcattc ttccgtcaag    2220
aaagtcaaaa acttctgcaa agcgataaaa acgcacggc tgagttagca aacggcgctc     2280
tcggtatgat tgagctaaac gatgattaca cactgaaaaa agtgatgaaa ccgctgattg    2340
catctaacac agtaacagat gaaattgaac gcgcgaacgt ctttaaaatg aacggcaaat    2400
ggtacctgtt cactgactcc cgcggatcaa aaatgacgat tgacggcatt acgtctaacg    2460
atatttacat gcttggttat gtttctaatt ctttaactgg cccatacaag ccgctgaaca    2520
```

```
aaactggcct tgtgttaaaa atggatcttg atcctaacga tgtaaccttt acttactcac    2580
acttcgctgt acctcaagcg aaaggaaaca atgtcgtgat tacaagctat atgacaaaca    2640
gaggattcta cgcagacaaa caatcaacgt ttgcgccaag cttcctgctg aacatcaaag    2700
gcaagaaaac atctgttgtc aaagacagca tccttgaaca aggacaatta acagttaaca    2760
aatagtgacc cggtcatgt ttgacagctt atcatcgata agctttaatg cggtagttta    2820
tcacagttaa attgctaacg cagtcaggca ccgtgtatga aatctaacaa tgcgctcatc    2880
gtcatcctcg gcaccgtcac cctggatgct gtaggcatag gcttggttat gccggtactg    2940
ccgggcctct tgcgggatat cgtccattcc gacagcatcg ccagtcacta tggcgtgctg    3000
ctagcgctat atgcgttgat gcaatttcta tgcgcacccg ttctcggagc actgtccgac    3060
cgctttggcc gccgcccagt cctgctcgct tcgctacttg gagccactat cgactacgcg    3120
atcatggcga ccacacccgt cctgtggatc ctctacgccg gacgcatcgt ggccggcatc    3180
accggcgcca caggtgcggt tgctggcgcc tatatcgccg acatcaccga tggggaagat    3240
cgggctcgcc acttcgggct catgagcgct tgtttcggcg tgggtatggt ggcaggcccc    3300
gtggccgggg gactgttggg cgccatctcc ttgcatgcac cattccttgc ggcggcggtg    3360
ctcaacggcc tcaacctact actgggctgc ttcctaatgc aggagtcgca taagggagag    3420
cgtcgaccga tgcccttgag agccttcaac ccagtcagct ccttccggtg ggcgcggggc    3480
atgactatcg tcgccgcact tatgactgtc ttctttatca tgcaactcgt aggacaggtg    3540
ccggcagcgc tctgggtcat tttcggcgag gaccgctttc gctggagcgc gacgatgatc    3600
ggcctgtcgc ttgcggtatt cggaatcttg cacgccctcg ctcaagcctt cgtcactggt    3660
cccgccacca aacgtttcgg cgagaagcag gccattatcg ccggcatggc ggccgacgcg    3720
ctgggctacg tcttgctggc gttcgcgacg cgaggctgga tggccttccc cattatgatt    3780
cttctcgctt ccggcggcat cgggatgccc gcgttgcagg ccatgctgtc caggcaggta    3840
gatgacgacc atcagggaca gcttcaagga tcgctcgcgg ctcttaccag cctaacttcg    3900
atcactggac cgctgatcgt cacggcgatt tatgccgcct cggcgagcac atggaacggg    3960
ttggcatgga ttgtaggcgc cgccctatac cttgtctgcc tccccgcgtt gcgtcgcggt    4020
gcatggagcc gggccacctc gacctgatag ctagcgtcga cactagctga taacctaggg    4080
ccagcaaaag gccaggaacc gtaaaaaggc cgcgttgctg gcgttttcc ataggctccg     4140 ccccctgac gagcatcaca aaatcgacg ctcaagtcag aggtggcgaa acccgacagg      4200
actataaaga taccaggcgt ttcccctgg aagctccctc gtgcgctctc ctgttccgac     4260
cctgccgctt accggatacc tgtccgcctt tctcccttcg ggaagcgtgg cgctttctca    4320
tagctcacgc tgtaggtatc tcagttcggt gtaggtcgtt cgctccaagc tgggctgtgt    4380
gcacgaaccc cccgttcagc ccgaccgctg cgccttatcc ggtaactatc gtcttgagtc    4440
caacccggta agacacgact tatcgccact ggcagcagcc actggtaaca ggattagcag    4500
agcgaggtat gtaggcggtg ctacagagtt cttgaagtgg tggcctaact acggctacac    4560
tagaaggaca gtatttggta tctgcgctct gctgaagcca gttaccttcg gaaaaagagt    4620
tggtagctct tgatccggca aacaaaccac cgctggtagc ggtggttttt tgtttgcaa     4680 gcagcagatt acgcgcagaa aaaaggatc tcaagaagat cctttgatct tttctacggg    4740
gtctgacgct cagtagatct aaaacactag gcccaagagt ttgtagaaac gcaaaaggc     4800 catccgtcag gatggccttc tgcttaattt gatgcctggc agtttatggc gggcgtcctg    4860
cccgccaccc tccgggccgt tgcttcgcaa cgttcaaatc cgctcccggc ggatttgtcc    4920
```

```
tactcaggag agcgttcacc gacaaacaac agataaaacg aaaggcccag tctttcgact    4980
gagcctttcg ttttatttga tgcctggcag ttccctactc tcgcatgggg agaccccaca    5040
ctaccatcgg cgctacggcg tttcacttct gagttcggca tggggtcagg tgggaccacc    5100
gcgctactgc cgccaggcaa attctgtttt atcagaccgc ttctgcgttc tgatttaatc    5160
tgtatcaggc tgaaaatctt ctctcatccg ccaaaacagc caagctggat ctggcaaatc    5220
gctgaatatt cctttttgtct ccgaccatca ggcacctgag tcgctgtctt tttcgtgaca   5280
ttcagttcgc tgcgctcacg gctctggcag tgaatggggg taaatggcac tacaggcgcc    5340
ttttatggat tcatgcaagg aaactaccca taatacaaga aaagcccgtc acgggcttct    5400
cagggcgttt tatggcgggt ctgctatgtg gtgctatctg acttttgct gttcagcagt     5460
tcctgccctc tgattttcca gtctgaccac ttcggattat cccgtgacag gtcattcaga    5520
ctggctaatg cacccagtaa ggcagcggta tcatcaacag gcttaccgt cttactgtca     5580
accggatcta aaacactagc ccaacctttc atagaaggcg cgtggaat cgaaatctcg      5640
tgatggcagg ttgggcgtcg cttggtcggt catttcgaac cccagagtcc cgctcagaag    5700
aactcgtcaa gaaggcgata gaaggcgatg cgctgcgaat cggagcggc gataccgtaa     5760
agcacgagga agcggtcagc ccattcgccg ccaagctctt cagcaatatc acgggtagcc    5820
aacgctatgt cctgatagcg gtccgccaca cccagccggc cacagtcgat gaatccagaa    5880
aagcggccat tttccaccat gatattcggc aagcaggcat cgccatgggt cacgacgaga    5940
tcctcgccgt cgggcatgcg cgccttgagc ctggcgaaca gttcggctgg cgcgagcccc    6000
tgatgctctt cgtccagatc atcctgatcg acaagaccgg cttccatccg agtacgtgct    6060
cgctcgatgc gatgtttcgc ttggtggtcg aatgggcagg tagccggatc aagcgtatgc    6120
agccgccgca ttgcatcagc catgatggat actttctcgg caggagcaag gtgagatgac    6180
aggagatcct gccccggcac ttcgcccaat agcagccagt cccttcccgc ttcagtgaca    6240
acgtcgagca cagctgcgca aggaacgccc gtcgtggcca gccacgatag ccgcgctgcc    6300
tcgtcctgca gttcattcag ggcaccggac aggtcggtct tgacaaaaag aaccgggcgc    6360
ccctgcgctg acagccggaa cacggcggca tcagagcagc cgattgtctg ttgtgcccag    6420
tcatagccga atagcctctc cacccaagcg gccggagaac ctgcgtgcaa tccatcttgt    6480
tcaatcatgc gaaacgatcc tcatcctgtc tcttgatcag atcttgatcc cctgcgccat    6540
cagatccttg gcggcaagaa agccatccag tttactttgc agggcttccc aaccttacca    6600
gagggcgccc cagctggcaa ttccggttcg ctgctagaca acatcagcaa ggagaaaggg    6660
gctaccggcg aaccagcagc cccttttataa aggcgcttca gtagtcagac cagcatcagt   6720
cctgaaaagg cgggcctgcg cccgcctcca ggttgctact taccggattc gtaagccatg    6780
aaagccgcca cctccctgtg tccgtctctg taacgaatct cgcacagcga ttttcgtgtc    6840
agataagtga atatcaacag tgtgagacac acgatcaaca cacaccagac aagggaactt    6900
cgtggtagtt tcatggcctt cttctccttg cgcaaagcgc ggtaagaggc tatcctgatg    6960
tggactagac atagggatgc ctcgtggtgg ttaatgaaaa ttaacttact acggggctat    7020
cttctttctg ccacacaaca cggcaacaaa ccaccttcac gtcatgaggc agaaagcctc    7080
aagcgccggg cacatcatag cccatatacc tgcacgctga ccacactcac tttccctgaa    7140
aataatccgc tcattcagac cgttcacggg aaatccgtgt gattgttgcc gcatcacgct    7200
gcctcccgga gtttgtctcg agcacttttg ttacccgcca aacaaacccc aaaaacaacc    7260
catacccaac ccaataaaac accaaaacaa gacaaataat cattgattga tggttgaaat    7320
```

-continued

```
gggtaaact tgacaaacaa acccacttaa aacccaaaac ataccaaaac acacaccaaa      7380
aaaacaccat aaggagtttt ataaatgttg gtattcattg atgacggttc aacaaacatc      7440
aaactacagt ggcaggaaag cgacggaaca attaaacagc acattagccc gaacagcttc      7500
aaacgcgagt gggcagtctc ttttggtgat aaaaaggtct ttaactacac actgaacggc      7560
gaacagtatt catttgatcc aatcagcccg gatgctgtag tcacaaccaa tatcgcatgg      7620
caatacagcg acgttaatgt cgttgcagtg catcacgcct tactgaccag tggtctgccg      7680
gtaagcgaag tggatattgt ttgcacactt cctctgacag agtattacga cagaaataac      7740
caacccaata cggaaaatat tgagcgtaag aaagcaaact tccggaaaaa aattacatta      7800
aatggcgggg atacattcac aataaaagat gtaaaagtca tgcctgaatc tataccggca      7860
ggttatgaag ttctacaaga actggatgag ttagattctt tattaattat agatctcggg      7920
ggcaccacat tagatatttc tcaggtaatg gggaaattat cggggatcag taaaatatac      7980
ggagactcat ctcttggtgt ctctctggtt acatctgcag taaaagatgc cctttctctt      8040
gcgagaacaa aaggaagtag ctatcttgct gacgatataa tcattcacag aaaagataat      8100
aactatctga gcaacgaat taatgatgag aacaaaatat caatagtcac cgaagcaatg      8160
aatgaagcac ttcgtaaact tgagcaacgt gtattaaata cgctcaatga atttctggt      8220 tatactcatg ttatggttat aggcggtggc gcagaattaa tatgcgatgc agtaaaaaaa      8280
cacacacaga ttcgtgatga acgttttttc aaaaccaata actctcaata tgatttagtt      8340
aacggtatgt atctcatagg taattaatga tggacaagcg cagaaccatt gccttcaaac      8400
taaatccaga tgtaaatcaa acagataaaa ttgtttgtga tacactggac agtatcccgc      8460
aaggggaacg aagccgcctt aaccgggccg cactgacggc aggtctggcc ttatacagac      8520
aagatccccg gaccccttc ctttatgtg agctgctgac gaaagaaacc acattttcag      8580
atatcgtgaa tatattgaga tcgctatttc caaaagagat ggccgattt aattcttcaa      8640 tagtcactca atcctcttca caacaagagc aaaaaagtga tgaagagacc aaaaaaaatg      8700
cgatgaagct aataaattaa ttcaattatt attgagttcc ctttatccac tatcaggctg      8760
gataaaggga actcaatcaa gttattttct taccagtcat tacataatcg ttattatgaa      8820
ataatcgttt gcactgtctc tgttattcag gcaatttcaa taaaggcact tgctcacgct      8880
ctgtcatttt ctgaaactct tcatgctg                                        8908
```

```
<210> SEQ ID NO 19
<211> LENGTH: 2253
<212> TYPE: DNA
<213> ORGANISM: Artificial Sequence
<220> FEATURE:
<223> OTHER INFORMATION: ClyA::SacB fusion gene
<220> FEATURE:
<221> NAME/KEY: CDS
<222> LOCATION: (1)..(2253)

<400> SEQUENCE: 19 atg act agt att ttt gca gaa caa act gta gag gta gtt aaa agc gcg      48
Met Thr Ser Ile Phe Ala Glu Gln Thr Val Glu Val Val Lys Ser Ala
1               5                   10                  15 atc gaa acc gca gat ggg gca tta gat ctt tat aac aaa tac ctc gac      96
Ile Glu Thr Ala Asp Gly Ala Leu Asp Leu Tyr Asn Lys Tyr Leu Asp
                20                  25                  30 cag gtc atc ccc tgg aag acc ttt gat gaa acc ata aaa gag tta agc     144
Gln Val Ile Pro Trp Lys Thr Phe Asp Glu Thr Ile Lys Glu Leu Ser
            35                  40                  45
```

| | | |
|---|---|---|
| cgt ttt aaa cag gag tac tcg cag gaa gct tct gtt tta gtt ggt gat | 192 | |
| Arg Phe Lys Gln Glu Tyr Ser Gln Glu Ala Ser Val Leu Val Gly Asp | | |
| 50          55               60 | | |
| att aaa gtt ttg ctt atg gac agc cag gac aag tat ttt gaa gcg aca | 240 | |
| Ile Lys Val Leu Leu Met Asp Ser Gln Asp Lys Tyr Phe Glu Ala Thr | | |
| 65              70              75              80 | | |
| caa act gtt tat gaa tgg tgt ggt gtc gtg acg caa tta ctc tca gcg | 288 | |
| Gln Thr Val Tyr Glu Trp Cys Gly Val Val Thr Gln Leu Leu Ser Ala | | |
|                 85              90              95 | | |
| tat att tta cta ttt gat gaa tat aat gag aaa aaa gca tca gcc cag | 336 | |
| Tyr Ile Leu Leu Phe Asp Glu Tyr Asn Glu Lys Lys Ala Ser Ala Gln | | |
|                    100             105             110 | | |
| aaa gac att ctc att agg ata tta gat gat ggt gtc aag aaa ctg aat | 384 | |
| Lys Asp Ile Leu Ile Arg Ile Leu Asp Asp Gly Val Lys Lys Leu Asn | | |
|            115             120             125 | | |
| gaa gcg caa aaa tct ctc ctg aca agt tca caa agt ttc aac aac gct | 432 | |
| Glu Ala Gln Lys Ser Leu Leu Thr Ser Ser Gln Ser Phe Asn Asn Ala | | |
|        130             135             140 | | |
| tcc gga aaa ctg ctg gca tta gat agc cag tta act aat gat ttt tcg | 480 | |
| Ser Gly Lys Leu Leu Ala Leu Asp Ser Gln Leu Thr Asn Asp Phe Ser | | |
| 145             150             155             160 | | |
| gaa aaa agt agt tat ttc cag tca cag gtg gat aga att cgt aag gaa | 528 | |
| Glu Lys Ser Ser Tyr Phe Gln Ser Gln Val Asp Arg Ile Arg Lys Glu | | |
|                 165             170             175 | | |
| gct tat gcc ggt gct gca gcc ggc ata gtc gcc ggt ccg ttt gga tta | 576 | |
| Ala Tyr Ala Gly Ala Ala Ala Gly Ile Val Ala Gly Pro Phe Gly Leu | | |
|                    180             185             190 | | |
| att att tcc tat tct att gct gcg ggc gtg att gaa ggg aaa ttg att | 624 | |
| Ile Ile Ser Tyr Ser Ile Ala Ala Gly Val Ile Glu Gly Lys Leu Ile | | |
|            195             200             205 | | |
| cca gaa ttg aat aac agg cta aaa aca gtg caa aat ttc ttt act agc | 672 | |
| Pro Glu Leu Asn Asn Arg Leu Lys Thr Val Gln Asn Phe Phe Thr Ser | | |
|        210             215             220 | | |
| tta tca gct aca gtg aaa caa gcg aat aaa gat atc gat gcg gca aaa | 720 | |
| Leu Ser Ala Thr Val Lys Gln Ala Asn Lys Asp Ile Asp Ala Ala Lys | | |
| 225             230             235             240 | | |
| ttg aaa tta gcc act gaa ata gca gca att ggg gag ata aaa acg gaa | 768 | |
| Leu Lys Leu Ala Thr Glu Ile Ala Ala Ile Gly Glu Ile Lys Thr Glu | | |
|                 245             250             255 | | |
| acc gaa aca acc aga ttc tac gtt gat tat gat gat tta atg ctt tct | 816 | |
| Thr Glu Thr Thr Arg Phe Tyr Val Asp Tyr Asp Asp Leu Met Leu Ser | | |
|                    260             265             270 | | |
| tta tta aaa gga gct gca aag aaa atg att aac acc tgt aat gaa tac | 864 | |
| Leu Leu Lys Gly Ala Ala Lys Lys Met Ile Asn Thr Cys Asn Glu Tyr | | |
|            275             280             285 | | |
| caa caa cgt cat ggt aag aag acg ctt ttc gag gtt cct gac gtc gct | 912 | |
| Gln Gln Arg His Gly Lys Lys Thr Leu Phe Glu Val Pro Asp Val Ala | | |
|        290             295             300 | | |
| agt aaa gaa acg aac caa aag cca tat aag gaa aca tac ggc att tcc | 960 | |
| Ser Lys Glu Thr Asn Gln Lys Pro Tyr Lys Glu Thr Tyr Gly Ile Ser | | |
| 305             310             315             320 | | |
| cat att aca cgc cat gat atg ctg caa atc cct gaa cag caa aaa aat | 1008 | |
| His Ile Thr Arg His Asp Met Leu Gln Ile Pro Glu Gln Gln Lys Asn | | |
|                 325             330             335 | | |
| gaa aaa tat caa gtt cct gaa ttc gat tcg tcc aca att aaa aat atc | 1056 | |
| Glu Lys Tyr Gln Val Pro Glu Phe Asp Ser Ser Thr Ile Lys Asn Ile | | |
|                    340             345             350 | | |
| tct tct gca aaa ggc ctg gac gtt tgg gac agc tgg cca tta caa aac | 1104 | |
| Ser Ser Ala Lys Gly Leu Asp Val Trp Asp Ser Trp Pro Leu Gln Asn | | |
|            355             360             365 | | |

```
gct gac ggc act gtc gca aac tat cac ggc tac cac atc gtc ttt gca      1152
Ala Asp Gly Thr Val Ala Asn Tyr His Gly Tyr His Ile Val Phe Ala
    370                 375                 380 tta gcc gga gat cct aaa aat gcg gat gac aca tcg att tac atg ttc      1200
Leu Ala Gly Asp Pro Lys Asn Ala Asp Asp Thr Ser Ile Tyr Met Phe
385                 390                 395                 400 tat caa aaa gtc ggc gaa act tct att gac agc tgg aaa aac gct ggc      1248
Tyr Gln Lys Val Gly Glu Thr Ser Ile Asp Ser Trp Lys Asn Ala Gly
                405                 410                 415 cgc gtc ttt aaa gac agc gac aaa ttc gat gca aat gat tct atc cta      1296
Arg Val Phe Lys Asp Ser Asp Lys Phe Asp Ala Asn Asp Ser Ile Leu
            420                 425                 430 aaa gac caa aca caa gaa tgg tca ggt tca gcc aca ttt aca tct gac      1344
Lys Asp Gln Thr Gln Glu Trp Ser Gly Ser Ala Thr Phe Thr Ser Asp
        435                 440                 445 gga aaa atc cgt tta ttc tac act gat ttc tcc ggt aaa cat tac ggc      1392
Gly Lys Ile Arg Leu Phe Tyr Thr Asp Phe Ser Gly Lys His Tyr Gly
    450                 455                 460 aaa caa aca ctg aca act gca caa gtt aac gta tca gca tca gac agc      1440
Lys Gln Thr Leu Thr Thr Ala Gln Val Asn Val Ser Ala Ser Asp Ser
465                 470                 475                 480 tct ttg aac atc aac ggt gta gag gat tat aaa tca atc ttt gac ggt      1488
Ser Leu Asn Ile Asn Gly Val Glu Asp Tyr Lys Ser Ile Phe Asp Gly
                485                 490                 495 gac gga aaa acg tat caa aat gta cag cag ttc atc gat gaa ggc aac      1536
Asp Gly Lys Thr Tyr Gln Asn Val Gln Gln Phe Ile Asp Glu Gly Asn
            500                 505                 510 tac agc tca ggc gac aac cat acg ctg aga gat cct cac tac gta gaa      1584
Tyr Ser Ser Gly Asp Asn His Thr Leu Arg Asp Pro His Tyr Val Glu
        515                 520                 525 gat aaa ggc cac aaa tac tta gta ttt gaa gca aac act gga act gaa      1632
Asp Lys Gly His Lys Tyr Leu Val Phe Glu Ala Asn Thr Gly Thr Glu
    530                 535                 540 gat ggc tac caa ggc gaa gaa tct tta ttt aac aaa gca tac tat ggc      1680
Asp Gly Tyr Gln Gly Glu Glu Ser Leu Phe Asn Lys Ala Tyr Tyr Gly
545                 550                 555                 560 aaa agc aca tca ttc ttc cgt caa gaa agt caa aaa ctt ctg caa agc      1728
Lys Ser Thr Ser Phe Phe Arg Gln Glu Ser Gln Lys Leu Leu Gln Ser
                565                 570                 575 gat aaa aaa cgc acg gct gag tta gca aac ggc gct ctc ggt atg att      1776
Asp Lys Lys Arg Thr Ala Glu Leu Ala Asn Gly Ala Leu Gly Met Ile
            580                 585                 590 gag cta aac gat gat tac aca ctg aaa aaa gtg atg aaa ccg ctg att      1824
Glu Leu Asn Asp Asp Tyr Thr Leu Lys Lys Val Met Lys Pro Leu Ile
        595                 600                 605 gca tct aac aca gta aca gat gaa att gaa cgc gcg aac gtc ttt aaa      1872
Ala Ser Asn Thr Val Thr Asp Glu Ile Glu Arg Ala Asn Val Phe Lys
    610                 615                 620 atg aac ggc aaa tgg tac ctg ttc act gac tcc cgc gga tca aaa atg      1920
Met Asn Gly Lys Trp Tyr Leu Phe Thr Asp Ser Arg Gly Ser Lys Met
625                 630                 635                 640 acg att gac ggc att acg tct aac gat att tac atg ctt ggt tat gtt      1968
Thr Ile Asp Gly Ile Thr Ser Asn Asp Ile Tyr Met Leu Gly Tyr Val
                645                 650                 655 tct aat tct tta act ggc cca tac aag ccg ctg aac aaa act ggc ctt      2016
Ser Asn Ser Leu Thr Gly Pro Tyr Lys Pro Leu Asn Lys Thr Gly Leu
            660                 665                 670 gtg tta aaa atg gat ctt gat cct aac gat gta acc ttt act tac tca      2064
Val Leu Lys Met Asp Leu Asp Pro Asn Asp Val Thr Phe Thr Tyr Ser
        675                 680                 685
```

```
cac ttc gct gta cct caa gcg aaa gga aac aat gtc gtg att aca agc       2112
His Phe Ala Val Pro Gln Ala Lys Gly Asn Asn Val Val Ile Thr Ser
    690                 695                 700 tat atg aca aac aga gga ttc tac gca gac aaa caa tca acg ttt gcg       2160
Tyr Met Thr Asn Arg Gly Phe Tyr Ala Asp Lys Gln Ser Thr Phe Ala
705                 710                 715                 720 cca agc ttc ctg ctg aac atc aaa ggc aag aaa aca tct gtt gtc aaa       2208
Pro Ser Phe Leu Leu Asn Ile Lys Gly Lys Lys Thr Ser Val Val Lys
                725                 730                 735 gac agc atc ctt gaa caa gga caa tta aca gtt aac aaa tag tga           2253
Asp Ser Ile Leu Glu Gln Gly Gln Leu Thr Val Asn Lys
            740                 745

<210> SEQ ID NO 20
<211> LENGTH: 749
<212> TYPE: PRT
<213> ORGANISM: Artificial Sequence
<220> FEATURE:
<223> OTHER INFORMATION: Synthetic Construct

<400> SEQUENCE: 20

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285
```

-continued

```
Gln Gln Arg His Gly Lys Lys Thr Leu Phe Glu Val Pro Asp Val Ala
    290                 295                 300

Ser Lys Glu Thr Asn Gln Lys Pro Tyr Lys Glu Thr Tyr Gly Ile Ser
305                 310                 315                 320

His Ile Thr Arg His Asp Met Leu Gln Ile Pro Glu Gln Gln Lys Asn
                325                 330                 335

Glu Lys Tyr Gln Val Pro Glu Phe Asp Ser Thr Ile Lys Asn Ile
            340                 345                 350

Ser Ser Ala Lys Gly Leu Asp Val Trp Asp Ser Trp Pro Leu Gln Asn
            355                 360                 365

Ala Asp Gly Thr Val Ala Asn Tyr His Gly Tyr His Ile Val Phe Ala
370                 375                 380

Leu Ala Gly Asp Pro Lys Asn Ala Asp Asp Thr Ser Ile Tyr Met Phe
385                 390                 395                 400

Tyr Gln Lys Val Gly Glu Thr Ser Ile Asp Ser Trp Lys Asn Ala Gly
                405                 410                 415

Arg Val Phe Lys Asp Ser Asp Lys Phe Asp Ala Asn Asp Ser Ile Leu
            420                 425                 430

Lys Asp Gln Thr Gln Glu Trp Ser Gly Ser Ala Thr Phe Thr Ser Asp
            435                 440                 445

Gly Lys Ile Arg Leu Phe Tyr Thr Asp Phe Ser Gly Lys His Tyr Gly
450                 455                 460

Lys Gln Thr Leu Thr Thr Ala Gln Val Asn Val Ser Ala Ser Asp Ser
465                 470                 475                 480

Ser Leu Asn Ile Asn Gly Val Glu Asp Tyr Lys Ser Ile Phe Asp Gly
                485                 490                 495

Asp Gly Lys Thr Tyr Gln Asn Val Gln Gln Phe Ile Asp Glu Gly Asn
            500                 505                 510

Tyr Ser Ser Gly Asp Asn His Thr Leu Arg Asp Pro His Tyr Val Glu
            515                 520                 525

Asp Lys Gly His Lys Tyr Leu Val Phe Glu Ala Asn Thr Gly Thr Glu
            530                 535                 540

Asp Gly Tyr Gln Gly Glu Glu Ser Leu Phe Asn Lys Ala Tyr Tyr Gly
545                 550                 555                 560

Lys Ser Thr Ser Phe Phe Arg Gln Glu Ser Gln Lys Leu Leu Gln Ser
                565                 570                 575

Asp Lys Lys Arg Thr Ala Glu Leu Ala Asn Gly Ala Leu Gly Met Ile
            580                 585                 590

Glu Leu Asn Asp Asp Tyr Thr Leu Lys Lys Val Met Lys Pro Leu Ile
            595                 600                 605

Ala Ser Asn Thr Val Thr Asp Glu Ile Glu Arg Ala Asn Val Phe Lys
610                 615                 620

Met Asn Gly Lys Trp Tyr Leu Phe Thr Asp Ser Arg Gly Ser Lys Met
625                 630                 635                 640

Thr Ile Asp Gly Ile Thr Ser Asn Asp Ile Tyr Met Leu Gly Tyr Val
                645                 650                 655

Ser Asn Ser Leu Thr Gly Pro Tyr Lys Pro Leu Asn Lys Thr Gly Leu
            660                 665                 670

Val Leu Lys Met Asp Leu Asp Pro Asn Asp Val Thr Phe Thr Tyr Ser
            675                 680                 685

His Phe Ala Val Pro Gln Ala Lys Gly Asn Asn Val Val Ile Thr Ser
690                 695                 700

Tyr Met Thr Asn Arg Gly Phe Tyr Ala Asp Lys Gln Ser Thr Phe Ala
705                 710                 715                 720
```

Pro Ser Phe Leu Leu Asn Ile Lys Gly Lys Lys Thr Ser Val Val Lys
            725                 730                 735

Asp Ser Ile Leu Glu Gln Gly Gln Leu Thr Val Asn Lys
            740                 745

<210> SEQ ID NO 21
<211> LENGTH: 921
<212> TYPE: DNA
<213> ORGANISM: Salmonella typhi

<400> SEQUENCE: 21

| | | | | | |
|---|---|---|---|---|---|
| atgactagta | ttttgcaga | acaaactgta | gaggtagtta | aaagcgcgat | cgaaaccgca | 60 |
| gatggggcat | tagatcttta | taacaaatac | ctcgaccagg | tcatcccctg | aagacccttt | 120 |
| gatgaaacca | taaaagagtt | aagccgtttt | aaacaggagt | actcgcagga | agcttctgtt | 180 |
| ttagttggtg | atattaaagt | tttgcttatg | gacagccagg | acaagtattt | tgaagcgaca | 240 |
| caaactgttt | atgaatggtg | tggtgtcgtg | acgcaattac | tctcagcgta | tattttacta | 300 |
| tttgatgaat | ataatgagaa | aaagcatca | gcccagaaag | acattctcat | taggatatta | 360 |
| gatgatggtg | tcaagaaact | gaatgaagcg | caaaaatctc | tcctgacaag | ttcacaaagt | 420 |
| ttcaacaacg | cttccggaaa | actgctggca | ttagatagcc | agttaactaa | tgattttcg | 480 |
| gaaaaagta | gttatttcca | gtcacaggtg | gatagaattc | gtaaggaagc | ttatgccggt | 540 |
| gctgcagccg | gcatagtcgc | cggtccgttt | ggattaatta | tttcctattc | tattgctgcg | 600 |
| ggcgtgattg | aagggaaatt | gattccagaa | ttgaataaca | ggctaaaaac | agtgcaaaat | 660 |
| ttctttacta | gcttatcagc | tacagtgaaa | caagcgaata | agatatcga | tgcggcaaaa | 720 |
| ttgaaattag | ccactgaaat | agcagcaatt | ggggagataa | aaacggaaac | cgaaacaacc | 780 |
| agattctacg | ttgattatga | tgatttaatg | cttctttat | taaaggagc | tgcaagaaa | 840 |
| atgattaaca | cctgtaatga | ataccaacaa | cgtcatggta | agaagacgct | tttcgaggtt | 900 |
| cctgacgtcg | ctagctgata | a | | | | 921 |

<210> SEQ ID NO 22
<211> LENGTH: 1102
<212> TYPE: DNA
<213> ORGANISM: Salmonella typhi

<400> SEQUENCE: 22

| | | | | | |
|---|---|---|---|---|---|
| ggaggtaata | ggtaagaata | ctttataaaa | caggtactta | attgcaattt | atatatttaa | 60 |
| agaggcaaat | gattatgacc | ggaatatttg | cagaacaaac | tgtagaggta | gttaaaagcg | 120 |
| cgatcgaaac | cgcagatggg | gcattagatc | tttataacaa | atacctcgac | caggtcatcc | 180 |
| cctggaagac | ctttgatgaa | accataaaag | agttaagccg | ttttaaacag | gagtactcgc | 240 |
| aggaagcttc | tgttttagtt | ggtgatatta | aagttttgct | tatggacagc | caggacaagt | 300 |
| attttgaagc | gacacaaact | gtttatgaat | ggtgtggtgt | cgtgacgcaa | ttactctcag | 360 |
| cgtatatttt | actatttgat | gaatataatg | agaaaaagc | atcagcccag | aaagacattc | 420 |
| tcattaggat | attagatgat | ggtgtcaaga | aactgaatga | agcgcaaaaa | tctctcctga | 480 |
| caagttcaca | agtttcaac | aacgcttccg | gaaaactgct | ggcattagat | agccagttaa | 540 |
| ctaatgattt | ttcggaaaaa | gtagttatt | ccagtcaca | ggtggataga | attcgtaagg | 600 |
| aagcttatgc | cggtgctgca | gccggcatag | tcgccggtcc | gtttggatta | attatttcct | 660 |
| attctattgc | tgcgggcgtg | attgaaggga | aattgattcc | agaattgaat | aacaggctaa | 720 |
| aaacagtgca | aaatttcttt | actagcttat | cagctacagt | gaaacaagcg | aataaagata | 780 |

-continued

| | |
|---|---|
| tcgatgcggc aaaattgaaa ttagccactg aaatagcagc aattggggag ataaaaacgg | 840 |
| aaaccgaaac aaccagattc tacgttgatt atgatgattt aatgctttct ttattaaaag | 900 |
| gagctgcaaa gaaaatgatt aacacctgta atgaatacca acaaagacac ggtaagaaga | 960 |
| cgcttttcga ggttcctgac gtctgataca ttttcattcg atctgtgtac ttttaacgcc | 1020 |
| cgatagcgta aagaaaatga gagacggaga aaaagcgata ttcaacagcc cgataaacaa | 1080 |
| gagtcgttac cgggctgacg ag | 1102 |

<210> SEQ ID NO 23
<211> LENGTH: 1102
<212> TYPE: DNA
<213> ORGANISM: Salmonella paratyphi

<400> SEQUENCE: 23

| | |
|---|---|
| ggaggcaata ggtaggaata agttataaaa caatagctta attgcaattt atatatttaa | 60 |
| agaggcaaat gattatgact ggaatatttg cagaacaaac tgtagaggta gttaaaagcg | 120 |
| cgatcgaaac cgcagatggg gcattagatt tttataacaa atacctcgac caggttatcc | 180 |
| cctggaagac ctttgatgaa accataaaag agttaagccg ttttaaacag gagtactcgc | 240 |
| aggaagcttc tgttttagtt ggtgatatta agttttgct tatggacagc caggataagt | 300 |
| attttgaagc gacacaaact gtttatgaat ggtgtggtgt cgtgacgcaa ttactctcag | 360 |
| cgtatatttt actatttgat gaatataatg agaaaaaagc atcagcgcag aaagacattc | 420 |
| tcatcaggat attagatgat ggcgtcaata aactgaatga agcgcaaaaa tctctcctgg | 480 |
| gaagttcaca agtttcaac aacgcttcag gaaaactgct ggcattagat agccagttaa | 540 |
| ctaatgattt ctcggaaaaa agtagttatt ccagtcaca ggtggataga attcgtaagg | 600 |
| aagcttatgc cggtgctgca gcaggcatag tcgccggtcc gtttggatta attatttcct | 660 |
| attctattgc tgcgggcgtg attgaaggga aattgattcc agaattgaat gacaggctaa | 720 |
| aagcagtgca aaatttcttt actagcttat cagtcacagt gaaacaagcg aataaagata | 780 |
| tcgatgcggc aaaattgaaa ttagccactg aaatagcagc aattggggag ataaaaacgg | 840 |
| aaaccgaaac aaccagattc tacgttgatt atgatgattt aatgctttct ttactaaaag | 900 |
| gagctgcaaa gaaaatgatt aacacctgta atgaatacca acaaaggcac ggtaagaaga | 960 |
| cgcttctcga ggttcctgac atctgataca ttttcattcg ctctgtttac ttttaacgcc | 1020 |
| cgatagcgtg aagaaaatga gagacggaga aaaagcgata ttcaacagcc cgataaacaa | 1080 |
| gagtcgttac cgggctggcg ag | 1102 |

<210> SEQ ID NO 24
<211> LENGTH: 904
<212> TYPE: DNA
<213> ORGANISM: Shigella flexneri

<400> SEQUENCE: 24

| | |
|---|---|
| atgactgaaa tcgttgcaga taaaacggta gaagtagtta aaaacgcaat cgaaaccgca | 60 |
| gatggagcat tagatcttta taataaatat ctcgatcagg tcatcccctg gcagaccttt | 120 |
| gatgaaacca taaagagtt aagtcgcttt aaacaggagt attcacaggc agcctccgtt | 180 |
| ttagtcggcg atattaaaac cttacttatg gatagccagg ataagtattt tgaagcaacc | 240 |
| caaacagtgt atgaatggtg tggtgttgcg acgcaattgc tcgcagcgta tattttgcta | 300 |
| tttgatgagt acaatgagaa gaaagcatcc gcccctcatt aaggtactgg atgacggcat | 360 |
| cacgaagctg aatgaagcgc aaaattccct gctggtaagc tcacaaagtt tcaacaacgc | 420 |

-continued

```
ttccgggaaa ctgctggcgt tagatagcca gttaaccaat gattttcag aaaaaagcag        480 ctatttccag tcacaggtag ataaaatcag gaaggaagcg tatgccggtg ccgcagccgg        540
tgtcgtcgcc ggtccatttg gtttaatcat ttcctattct attgctgcgg gcgtagttga        600
agggaaactg attccagaat tgaagaacaa gttaaaatct gtgcagagtt tctttaccac        660
cctgtctaac acggttaaac aagcgaataa agatatcgat gccgccaaat tgaaattaac        720
caccgaaata gccgccatcg gggagataaa aacggaaact gaaaccacca gattctatgt        780
tgattatgat gatttaatgc tttctttgct aaaagcagcg gccaaaaaaa tgattaacac        840
ctgtaatgag tatcagaaaa gacacggtaa aagacactc tttgaggtac ctgaagtctg        900
ataa                                                                    904

<210> SEQ ID NO 25
<211> LENGTH: 1080
<212> TYPE: DNA
<213> ORGANISM: Escherichia coli

<400> SEQUENCE: 25
agaaataaag acattgacgc atcccgcccg gctaactatg aattagatga agtaaaattt         60
attaatagtt gtaaaacagg agtttcatta caatttatat atttaaagag gcgaatgatt        120
atgactgaaa tcgttgcaga taaaacggta gaagtagtta aaaacgcaat cgaaaccgca        180
gatggagcat tagatcttta taataaatat ctcgatcagg tcatcccctg gcagaccttt        240
gatgaaacca taaagagtt aagtcgcttt aaacaggagt attcacaggc agcctccgtt        300
ttagtcggcg atattaaaac cttacttatg gatagccagg ataagtattt tgaagcaacc        360
caaacagtgt atgaatggtg tggtgttgcg acgcaattgc tcgcagcgta tattttgcta        420
tttgatgagt acaatgagaa gaaagcatcc gcccagaaag acattctcat taaggtactg        480
gatgacggca tcacgaagct gaatgaagcg caaaaatccc tgctggtaag ctcacaaagt        540
ttcaacaacg cttccgggaa actgctggcg ttagatagcc agttaaccaa tgattttca        600 gaaaaaagca gctatttcca gtcacaggta gataaaatca ggaaggaagc atatgccggt        660
gccgcagccg gtgtcgtcgc cggtccattt ggattaatca tttcctattc tattgctgcg        720
ggcgtagttg aaggaaaact gattccagaa ttgaagaaca gttaaaatc tgtgcagaat        780 ttctttacca ccctgtctaa cacggttaaa caagcgaata agatatcga tgccgccaaa        840 ttgaaattaa ccaccgaaat agccgccatc ggtgagataa aaacggaaac tgaaacaacc        900
agattctacg ttgattatga tgatttaatg ctttctttgc taaaagaagc ggccaaaaaa        960
atgattaaca cctgtaatga gtatcagaaa agacacggta aaagacact ctttgaggta      1020 cctgaagtct gataagcgat tattctctcc atgtactcaa ggtataaggt ttatcacatt      1080
```

METHODS FOR ELICITING AN IMMUNE RESPONSE USING CYTOLYSIN AND HEMOLYSIN FUSION PROTEINS

RELATED APPLICATIONS

This application is a Divisional of U.S. application Ser. No. 09/993,292, filed Nov. 23, 2001, now issued as U.S. Pat. No. 7,056,700 on Jun. 6, 2006 which claims priority to U.S. Provisional Patent Application No. 60/252,516, filed Nov. 22, 2000; each of which is hereby incorporated by reference in their entirety.

GOVERNMENT SUPPORT

The protein export system defined herein was developed through support from grants 5 RO1 AI29471, RO1 AI40297, and Research Contract NO1 AI45251 (M.M. Levine, Principal Investigator), from the National Institutes of Health. The U. S. Goverment has certain rights in this invention.

BACKGROUND OF THE INVENTION

1. Field of the Invention

The disclosure below relates to the use of a protein export system. The disclosed system provides effective methods and compositions useful for the production of recombinant proteins.

2. Description of the Related Art

Protein expression systems have long used high copy number expression plasmids or expression vectors in an attempt to increase yields of recombinant proteins of interest. High copy number expression plasmids and the proteins of interest they encode can exert a negative effect on the fitness of a host containing an expression plasmid. The notable burden placed upon prokaryotic host cells carrying multicopy plasmids is the cumulative result of a metabolic cascade triggered by two processes: 1) the replication and maintenance of expression plasmids and 2) transcription and translation of the various plasmid-encoded functions including the gene of interest. Such mechanisms could explain the observation that plasmid-bearing bacteria grow slower than plasmid-less bacteria. This burden can also explain the observation that growth rate decreases as copy number increases.

As the gene of interest is expressed, the growth rate of the recombinant host cell decreases. The decrease in growth rate may trigger the induction of various cellular proteases that can degrade recombinantly produced protein present in cytoplasm of the host cell. Reduced growth rate is therefore the inevitable consequence of metabolic burden, which in turn is the cumulative result of a number of physiological perturbations. Because this reduction in the growth rate creates a selective pressure for loss of resident plasmids in the absence of selection, significant loss of expression plasmids from the host cell carrying an expression vector may occur after transformation of the host cell.

Host cells with reduced growth rates can spontaneously shed an expression plasmid to remove from the host cell an unnecessary metabolic burden and allow plasmid-less host cells to quickly outgrow the population of plasmid-bearing host cells. Such a shift in protein expression within a population of host cells would be expected to reduce the protein production.

Accordingly, it would be desirable to prepare a protein expression system that would optimize protein expression from the expression vector while minimizing the metabolic burden on the host cell generated by the expression vector.

SUMMARY OF THE INVENTION

The disclosed material relates to the use of an export protein to facilitate export of a fusion protein out of a host cell. One disclosed embodiment provides a method for expressing a gene in a bacterial cell comprising providing an expression vector to a population of untransformed bacterial host cells, wherein the expression vector comprises an expression cassette comprising an export protein coding sequence genetically fused to a protein of interest coding sequence, expressing the expression cassette such that an export protein::protein of interest fusion protein is produced and exported or transported into the culture medium.

Another disclosed embodiment relates to a method for eliciting an immune response from an animal comprising providing to an animal a population of bacterial host cells transformed with an expression vector which comprises an expression cassette comprising an export protein coding sequence genetically fused to a protein of interest coding sequence, expressing the expression cassette such that an export protein::protein of interest fusion protein is produced and exported or transported into the animal, and eliciting an immune response from the animal against the fusion protein.

Another disclosed embodiment relates to a system for expressing a protein of interest comprising: an expression vector comprising an expression cassette, wherein the expression cassette comprises an export protein coding sequence genetically fused to a protein of interest coding sequence, a host cell transformed with the expression vector, and a culturing environment for the transformed host cell, wherein the expression cassette expresses an export protein::protein of interest fusion protein, which is exported out of the transformed host cell.

BRIEF DESCRIPTION OF THE DRAWINGS

FIG. 1A illustrates pSEC84 expression vector. FIG. 1B illustrates pSEC84bla expression vector. FIG. 1C illustrates pSEC84sacB. FIG. 1D illustrates pSEC84gfpuv.

FIG. 2 illustrates exportation of ClyA-SacB protein fusion which results in the metabolisis of sucrose in solid growth medium. The strains were grown on media containing either 8% sucrose (2A and 2B), 16% sucrose (2C and 2D), or 8% sucrose+8% L-arabinose (2E and 2F). FIGS. 2A, 2C, and 2E demonstrate the growth of CVD 908-htrA expressing ClyA. FIGS. 2B, 2D, and 2F demonstrate the growth of CVD 908-htrA expressing ClyA-SacB.

DETAILED DESCRIPTION OF THE PREFERRED EMBODIMENT

Figure 1:
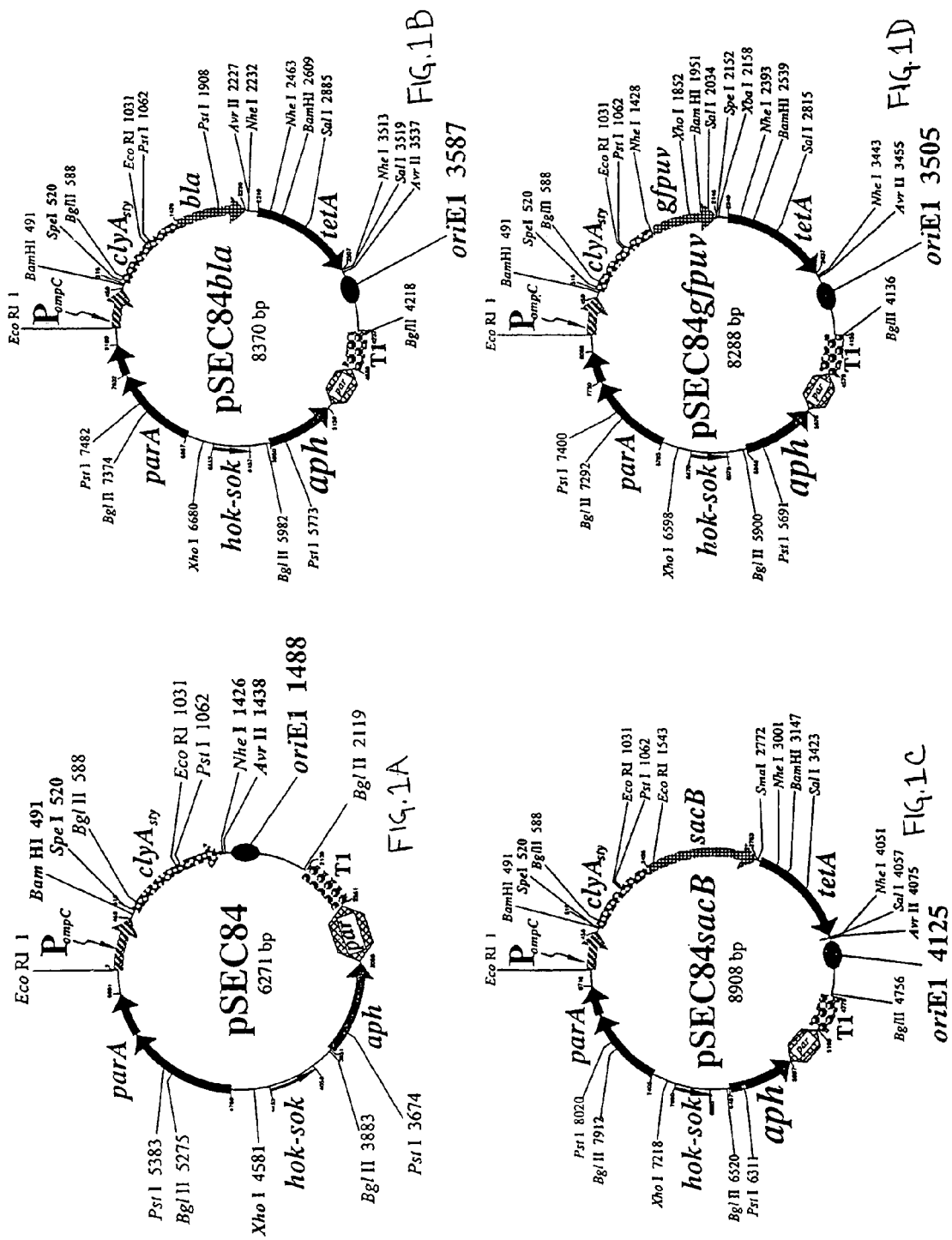
FIG. 1 provides examples of the expression vector of this invention.

The disclosure below provides a protein export system for efficiently producing recombinant protein from a bacterial host. In a preferred embodiment, the protein export system utilizes protein export machinery endogenous to the host bacterium into which the protein export system vector is introduced.

The protein export system has a number of useful applications. The system can be used to efficiently produce recombinant proteins of interest inside a bacterial host cell and export the recombinant protein of interest from the bacterial host cell. For example, the disclosed system can be used to efficiently produce recombinant proteins of interest in a bioreactor.

The protein export system can be also be used to provide to an animal antigenic material against which an immune response may be mounted. For example, in one embodiment an attenuated bacterium, such as *Salmonella*, is transformed with the components of the protein export system. The recombinant *Salmonella* can then be used as a live vector immunogenic composition capable of facilitating the generation of an immune response in an animal. The protein export system can be used with a variety of antigens of interest. Specific embodiments include immunogenic compositions directed against typhoid fever and other diseases. Immunogenic compositions expressing antigens that are exported from recombinant bacteria with a minimum of bacterial lysis are also disclosed.

A. HlyE Family Protein Export System

The disclosure below relates to the use of members of the HlyE family in a protein export system to facilitate protein expression. Members of the HlyE family can be used to facilitate the export of recombinantly produced proteins from their bacterial hosts. Expression systems that export recombinantly produced proteins are believed to facilitate increased protein production. The disclosed protein export system can also be used to prepare immunogenic compositions with which to vaccinate animals.

Growth rates of recombinant organisms containing expression vectors have been observed to decrease as the level of expression of a gene of interest increases. The decrease in growth may trigger the induction of various cellular proteases that can degrade the expressed recombinant protein. Reduced growth rate is therefore the inevitable consequence of metabolic burden, which, in turn, is the cumulative result of a number of physiological perturbations. For example, physiological perturbations result from the expression and accumulation of the protein of interest inside the host bacterium. This accumulation can be harmful to the viability of the host bacterium and thus a negative selection pressure.

Because metabolic burdens such as those discussed above create a selective pressure for loss of resident expression vectors in the absence of selection, significant loss of expression vector from the host bacterium can occur after the host bacterium has been transformed with the expression vector containing the gene of interest. Spontaneous plasmid loss removes any metabolic burden from the host bacteria and allows plasmid-less bacteria to quickly outgrow the population of plasmid-bearing bacteria. The overgrowth of bacterial cells that do not contain the expression vector and thus do not express the protein of interest reduces overall protein production levels. Therefore, host bacteria that are not genetically constrained to maintain expression vectors directing the synthesis of high levels of a given protein of interest may produce significantly less protein.

A preferred embodiment for exporting the recombinantly expressed protein of interest comprises exploiting an endogenous export system in the host bacteria containing the expression vector. Exploitation of an endogenous export system is advantageous in part because it avoids the need for large amounts of heterologous DNA encoding exotic proteins to supply an exogenous export system. Nevertheless, protein export systems utilizing exogenous export systems are also encompassed by the present disclosure.

An attractive endogenous export system candidate is the cryptic hemolysin encoded by Cytolysin A (clyA) within the chromosome of *Salmonella enterica* serovar Typhi (hereinafter "*S*. Typhi"), a member of the HlyE family of proteins. The HlyE family consists of a single protein, HlyE, and its close homologs from *E. coli*, *Shigella flexneri* and *S. Typhi*, and other bacteria. The *E. coli* protein is a functionally well characterized, pore-forming, chromosomally-encoded hemolysin also called ClyA, HlyE, and silent hemolysin A (SheA). It consist of 303 amino acid residues (34 kDa). Its transcription is positively controlled by SlyA, a regulator found in several enteric bacteria. HlyE forms stable, moderately cation-selective transmembrane pores with a diameter of 2.5-3.0 nm in lipid bilayers. The protein binds cholesterol, and pore formation in a membrane is stimulated if the membrane contains cholesterol. The crystal structure of *E. coli* HlyE has been solved to 2.0 Å resolution, and visualization of the lipid-associated form of the toxin at low resolution has been achieved by electron microscopy. The structure exhibits an elaborate helical bundle some 100 Å long. It oligomerizes in the presence of lipid to form transmembrane pores.

B. Cytolysin A (ClyA) Protein Export System

A preferred embodiment of the present disclosure relates to the use of the ClyA protein, a member of the HlyE family, in a protein export system. An approximately 1 kb clyA gene was cloned from *S. Typhi* CVD 908-htrA for use in a protein export system. The ClyA protein is exported from both *E. coli* and *S. Typhi* and is capable of exporting passenger proteins that have been genetically fused to the 3'-terminus of the clyA open reading frame. Passenger protein referred to herein is also referred to as a protein of interest. It is demonstrated that the proper folding of these fusion proteins occurs such that the inherent biological activity of the domains involved is observed.

Cytolysin A (ClyA) from *S. Typhi* was first described by Wallace et al. who also reported the crystal structure for the homologous hemolysin from *E. coli*. (Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.) This hemolysin has been described previously and variously referred to as ClyA, HlyE, or SheA. To avoid confusion, the *E. coli* hemolysin is referred to herein as HlyE and is encoded by hlyE. Also for clarity, the *S. Typhi* hemolysin is referred to herein as ClyA, which is encoded by clyA.

For illustrative purposes, the protein structure of the HlyE family members is discussed referring to the *E. coli* protein HlyE. HlyE is a kinked rod-shaped molecule with a hydrophobic 27 residue transmembrane region. This region comprises one terminus of the folded molecule and is proposed to form a pore within a target membrane. The formation of the pore ultimately leads to lysis of the target cell. In elegant electron microscopy studies, Wallace et al. showed that HlyE inserts into lipid vesicles to form pores comprised of 8 HlyE monomers.

Although the pore formation facilitated by HlyE has been elucidated, the mechanism by which HlyE and HlyE homologs are exported out of a bacterium remains unclear. Moreover, the manner by which the hemolysin inserts into target membranes for assembly into pores is also not well understood. Del Castillo et al., described the growth-phase dependent secretion of hemolytic activity which peaked during mid-log phase and vanished at the onset of stationary phase. (del Castillo, F. J., S. C. Leal, F. Moreno, and I. del Castillo. 1997. The *Escherichia coli* K-12 sheA gene encodes a 34-kDa secreted haemolysin. Mol. Microbiol. 25:107-115.) Ludwig and colleagues have reported that secretion of this cryptic hemolysin is accompanied by leakage of periplasmically confined proteins, but is not accompanied by loss of cytoplasmic proteins, arguing against outright cell lysis to release HlyE. (Ludwig, A., S. Bauer, R. Benz, B. Bergmann, and W. Goebel. 1999. Analysis of the SlyA-controlled expression, subcellular localization and pore-forming activity of a 34 kDa haemolysin (ClyA) from *Escherichia coli* K-12. Mol. Microbiol. 31:557-567.)

In addition, when compared to the sequence encoded by hlyE, N-terminal sequencing of secreted HlyE revealed that HlyE is not N-terminally processed during transport. Oscarsson et al., reported that HlyE binds to cholesterol and that the presence of cholesterol in target membranes stimulates pore formation and lysis. (Oscarsson, J., Y. Mizunoe, L. Li, X. Lai, A. Wieslander, and B. E. Uhlin. 1999. Molecular analysis of the cytolytic protein ClyA (SheA) from *Escherichia coli*. Mol. Microbiol. 32:1226-1238.) It is estimated that ~$10^3$ molecules of HlyE are required for lysis of a target erythrocyte suggesting significant accumulation of HlyE prior to detection of cell lysis. HlyE is remarkably stable within a range of pH values between 3.0 and 9.0, and is resistant to cleavage by proteases including trypsin and pepsin. (Atkins, A., N. R. Wybom, A. J. Wallace, T. J. Stillman, L. K. Black, A. B. Fielding, M. Hisakado, P. J. Artymiuk, and J. Green. 2000. Structure-function relationships of a novel bacterial toxin, hemolysin E. The role of $α_G$. J. Biol. Chem. 275:41150-41155.)

The nucleotide and amino acid sequence for the isolated clyA gene and ClyA protein used in the disclosed work are provided as SEQ ID NO:21 and SEQ ID NO:2, respectively. Other HlyE family members are also available and known to those of ordinary skill in the art. For example, another *S. Typhi* clyA gene for cytolysin A is available under GENBANK Accession No. AJ313034 (SEQ ID NO:22); *Salmonella paratyphi* clyA gene sequence for cytolysin A is available under GENBANK Accession No. AJ313033 (SEQ ID NO:23); the *Shigella flexneri* truncated HlyE (hlyE) gene's complete coding sequence is available under GENBANK Accession No. AF200955 (SEQ ID NO:24); and the *Escherichia coli* hlyE gene sequence is available under GENBANK Accession No. AJ001829 (SEQ ID NO:25).

The HlyE family of proteins typically cause hemolysis in target cells. Hemolytically active or inactive HlyE family members can both be used with the disclosed teachings. For example, it is known that mutation of the hlyE gene can reduce or eliminate hemolytic activity. For example, loss of hemolytic activity has been reported when hlyE is mutated such that amino acid substitutions occur at positions 180, 185, 187, and 193. Specifically, G180V, V185S, A187S, and I193S result in a loss of hemolytic activity from a HlyE protein expressed from a mutated hlyE gene.

The present disclosure utilizes the export characteristics of the HlyE family of proteins to produce a protein export system. For example, fusion proteins comprising any member of the HlyE family and a protein of interest are disclosed. More specifically, fusion proteins comprising ClyA and a protein of interest are disclosed. As discussed below, ClyA-containing fusion proteins are exported from the bacterial host cell and into the surrounding medium. This feature of the expression system comprising an export protein::protein of interest fusion protein component which facilitates production of the protein of interest and exportation of the export protein::protein of interest fusion protein.

Export Protein Expression Vectors

The protein export system described herein can be used to express and export a wide variety of fusion proteins comprising an export protein and a protein of interest. The export protein is selected from the HlyE family of proteins. In one embodiment, the protein of interest is encoded by a gene of interest. The gene of interest can be foreign to the bacteria containing the protein export system or it can be a gene that is endogenous to the bacteria. Typically, an export protein::protein of interest fusion protein construct is present in an expression cassette, which in turn is present in an expression vector. Each of these units are discussed below.

Expression Vectors

The protein export system utilizes an expression vector to facilitate the recombinant production of the protein of interest. Typically the expression vector will comprise an origin of replication and other structural features that control and regulate the maintenance of the expression vector in the host cell. By definition, the term "expression vector" refers to a plasmid, virus or other vehicle known in the art that has been manipulated by insertion or incorporation of the expression cassette comprising the export protein::protein of interest fusion protein expression cassette. An example of an expression vector system which teaches expression vectors that confer plasmid stability at two independent levels as described in Galen, et al., Immun. 67:6424-6433 (1999) and in U.S. patent application Ser. No. 09/204,117, filed Dec. 2, 1998 and Ser. No. 09/453,313, filed Dec. 2, 1999, which are hereby incorporated by reference in their entirety.

Export Protein-Fusion Protein Expression Cassettes

The protein export system described herein can be used to express and export a wide variety of fusion proteins comprising an export protein and a protein of interest. The protein of interest is encoded by the protein of interest coding sequence which is also the gene of interest. The gene of interest can be foreign to the bacteria containing the protein export system or it can be a gene that is endogenous to the bacteria. The protein of interest can range from a single amino acid to proteins several times the size of the export protein molecule. More preferably, the protein of interest can range from ten amino acids to two times the size of the export protein. It is preferrable that the size of the protein of interest be such that it not interfere with the ability of the export protein to be exported entirely out of the bacterium. Exemplary proteins of interest are from 0 kDa to at least 50 kDa in mass. Greater masses, and thus longer proteins may also be used as proteins of interest. For example, the proteins of interest may have a mass of 55 kDa, 60 kDa, 65 kDa, 70 kDa, 75 kDa, 80 kDa, 85 kDa, 90 kDa, 95 kDa, 100 kDa, or larger.

Alternatively, the protein of interest can consist of 1 to 1000 amino acids, or more. For example, the protein of interest may have 10, 20, 30, 40, 50, 60, 70, 80, 90, 100, 150, 200, 250, 300, 350, 400, 450, 500, 550, 600, 650, 700, 750, 800, 850, 900, 950, 1000 amino acids, or more.

Typically, the gene of interest to be expressed is present in an expression cassette. An expression cassette will typically contain suitable structural features, such as a promoter, terminator, etc., to permit transcription of the gene of interest.

Polynucleotide sequences encoding an export protein::protein of interest fusion protein (also known as "export protein::protein of interest fusion protein coding sequences") can be operatively linked to expression control sequences to form an expression cassette. The term "operatively linked"

refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, transcription terminators, optimized ribosome binding sequences, a start codon (i.e., ATG) in front of a protein-encoding gene, the correct reading frame of that gene to permit proper translation of mRNA, and stop codons. The term "control sequences" is intended to include, at a minimum, components whose presence can influence expression, and can also include additional components whose presence is advantageous, for example, leader sequences . Expression control sequences can include a promoter.

A "promoter" is the minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the export protein::protein of interest fusion protein coding sequence. Both constitutive and inducible promoters are useful with the disclosed methods. The expression of export protein::protein of interest fusion protein coding sequences can be driven by a number of promoters. Although the endogenous promoter of an export protein can be utilized for transcriptional regulation of the expression cassette, preferably, the promoter is a foreign regulatory sequence. An example of an inducible endogenous promoter is the ompC promoter which can be used to drive transcription of the expression cassette.

Promoters useful in the invention include both constitutive and inducible natural promoters as well as engineered promoters. A preferred inducible promoter should 1) provide low expression in the absence of the inducer; 2) provide high expression in the presence of the inducer; 3) use an induction scheme that does not interfere with the normal physiology of the host cell; and 4) have little or no effect on the expression of other genes. Examples of inducible promoters include those induced by chemical means. Those of skill in the art will know other promoters, both constitutive and inducible.

The particular promoter selected should be capable of causing sufficient expression to result in the production of an effective amount of the export protein: :protein of interest fusion protein. The effective amount of export protein::protein of interest fusion protein can vary depending on the goal of the expression. The promoters used in the vector constructs of the present disclosure can be modified, if desired, to affect their control characteristics.

The export protein::protein of interest fusion protein comprising the export protein and the protein of interest can further comprise purification tags engineered into the expression cassette to be expressed as a part of the export protein:: protein of interest fusion protein. The tag is chosen to facilitate purification of the export protein::protein of interest fusion protein and/or the protein of interested produced by the described methods. For example, a plurality of histidine residues can be engineered into the C-terminal portion or N-terminal portion of the protein of intereset to facilitate protein purification. It is preferable that the introduction of the tag minimizes improper folding of the protein of interest.

In addition to the polyhistidine tag, there are a number of other protein tags that can be used to facilitate protein purification. For example, antigenic tags such as the maltose binding protein tag, a c-myc epitope tag, a green fluorescent protein tag, a luciferace tag, a beta-galactosidase tag, a polyhistidine tag, or any other suitable protein expression tag that can be used with the described system.

The export protein::protein of interest fusion protein comprising the export protein and the protein of interest can further comprise additional features to facilitate the use of the expressed and exported protein. For example, protease recognition sites can be engineered between various components of export protein:protein of interest fusion protein, including, if applicable, the tags described above, to promote the separation of the components of the export protein::protein of interest fusion protein. For example, a protease recognition site can be introduced between the export protein and protein of interest sequences in the expression cassette. Also a protease recognition site can be introduced between the tag and the protein of interest sequences in the expression cassette. These protease recognition sites facilitate the separation of the export protein from the protein of interest.

Optionally, a selectable marker may be associated with the expression cassette. As used herein, the term "marker" refers to a gene encoding a trait or a phenotype that permits the selection of, or the screening for, a host cell containing the marker. The marker gene may be an antibiotic resistance gene whereby the appropriate antibiotic can be used to select for transformed host cells from among cells that are not transformed or the marker gene may be some other drug resistance gene. Examples of suitable selectable markers include adenosine deaminase, dihydrofolate reductase, hygromycin-B-phosphotransferase, thymidine kinase, xanthine-guanine phospho-ribosyltransferase, glyphosphate and glufosinate resistance and amino-glycoside 3'-O-phosphotransferase II (kanamycin, neomycin and G418 resistance). Those of skill in the art will know other suitable markers that can be employed with the disclosed teachings.

An example of an expression vector is shown in FIG. 1. In FIG. 1A, the pSEC84 expression vector is shown. The nucleotide sequence of the pSEC84 vector can be found at SEQ ID NO:1. The amino acid sequence of ClyA encoded by the clyA gene is found at SEQ ID NO:2.

Each vector shown in FIGS. 1A-D comprises a promoter ($P_{ompC}$-a modified osmotically controlled ompC promoter from *E. coli*), an export protein (clyA), an origin of replication, a transcriptional terminator (T1), a passive partitioning function (par), resistance to kanamycin (aph), a post-segregational killing system (hok-sok), and an active partitioning system (parA). It should be noted that these vector components are merely exemplary of a single embodiment of the disclosed system.

FIG. 1B illustrates the pSEC84bla expression vector. This expression vector contains the same features as the pSEC84 vector and further comprises a export protein::protein of interest fusion protein construct. Specifically, the bla gene encoding β-lactamase was cloned into the pSEC84 vector at the Nhe I site at position 1426 of the parent vector. Other fusion constructs are shown in FIG. 1C (pSEC84sacB) and FIG. 1D (pSEC84gfpuv).

Genes of Interest

The protein export system disclosed herein can be used with a variety of genes of interest. In one embodiment, the gene of interest encodes a desired protein. Any protein amenable to recombinant bacterial expression can be used with the disclosed export system. The gene of interest can encode for any polypeptide such as, for example, a mammalian polypeptide such as an enzyme, an enzyme inhibitor, a hormone, a lymphokine, a plasminogen activator, or any other protein of interest. The gene of interest can encode a eucaryotic gene, a procaryotic gene, a plant gene, or viral gene of interest.

One advantage of the disclosed system is that it provides a method by which proteins that were toxic to a host bacterium can now be expressed. For example, recombinant expression of certain proteins is complicated or impossible when the expressed protein is not exported from the host bacterial cell. With the methods disclosed herein, one of ordinary skill in the art could express a previously unexpressible or underexpressed protein to produce the desired protein in usable quantities.

In another embodiment, the gene of interest is an immunogenic antigen-encoding gene, and the protein of interest is an antigen which may be a protein or antigenic fragment thereof from any pathogen, such as viral pathogens, bacterial pathogens, and parasitic pathogens. Alternatively, the gene of interest may be a synthetic gene, constructed using recombinant DNA methods, which encode antigens or parts thereof from viral, bacterial, parasitic pathogens, or another antigen of interest. These pathogens can be infectious in humans, domestic animals or wild animal hosts.

Examples of particular viral pathogens, from which the viral antigens are derived, include, but are not limited to, Orthomyxoviruses, such as influenza virus; Retroviruses, such as Rous sarcoma virus (RSV) and simian immunodeficiency virus (SIV), Herpesviruses, such as Epstein Barr virus (EBV); cytomegalovirus (CMV) or herpes simplex virus; Lentiviruses, such as human immunodeficiency virus; Rhabdoviruses, such as rabies; Picomoviruses, such as poliovirus; Poxviruses, such as vaccinia; Rotavirus; and Parvoviruses.

Examples of immunogenic antigens from viral pathogens include the human immunodeficiency virus antigens Nef, p24, gp120, gp41, Tat, Rev, and Pol. Additional examples of antigens include the T cell and B cell epitopes of gp120, the hepatitis B surface antigen, rotavirus antigens, such as VP4, VP6, and VP7, influenza virus antigens such as hemagglutinin or nucleoprotein, and herpes simplex virus thymidine kinase. The nucleic acid and amino acid sequences for each of these virus antigens are well known in the art and readily available.

Bacterial pathogens, from which the bacterial antigens can be derived, include, but are not limited to, *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., and *Borellia burgdorferi.*

Examples of immunogenic antigens of bacterial pathogens include, but are not limited to, the *Shigella sonnei* form 1 antigen, the O-antigen of *V. cholerae* Inaba strain 569B, immunogenic antigens of enterotoxigenic *E. coli*, such as the CFA/I fimbrial antigen, and the nontoxic B-subunit of the heat-labile toxin, pertactin of *Bordetella pertussis*, adenylate cyclase-hemolysin of *B. pertussis*, and fragment C of tetanus toxin of *Clostridium tetani.*

Examples of immunogenic antigens of parasitic pathogens, from which the parasitic antigens can be derived, include, but are not limited to, *Plasmodium* spp., *Trypanosome* spp., *Giardia* spp., *Boophilus* spp., *Babesia* spp., *Entamoeba* spp., *Eimeria* spp., *Leishmania* spp., *Schistosome* spp., *Brugia* spp., *Fascida* spp., *Dirofilaria* spp., *Wuchereria* spp., and *Onchocerea* spp.

Examples of immunogenic antigens of parasitic pathogens include, but are not limited to, the circumsporozoite antigens of *Plasmodium* spp., such as the circumsporozoite antigen of *P. bergerii* or the circumsporozoite antigen of *P. falciparum*; the merozoite surface antigen of *Plasmodium* spp.; the galactose specific lectin of *Entamoeba histolytica*, gp63 of *Leishmania* spp., paramyosin of *Brugia malayi*, the triose-phosphate isomerase of *Schistosoma mansoni*; the secreted globin-like protein of *Trichostrongylus colubriformis*; the glutathione-S-transferase of *Frasciola hepatica, Schistosoma bovis* and *S. japonicum*; and KLH of *Schistosoma bovis* and *S. japonicum.*

In another embodiment, the gene of interest can encode a therapeutic agent, such as, but not limited to, tumor-specific, transplant, or autoimmune antigens or parts thereof. Alternatively, the gene of interest can encode synthetic genes, which encode for tumor-specific, transplant, or autoimmune antigens or parts thereof.

Examples of tumor specific antigens include prostate specific antigen, TAG-72 and CEA, MAGE-1 and tyrosinase. Recently it has been shown in mice that immunization with non-malignant cells expressing a tumor antigen provides a vaccine-type effect, and also helps the animal mount an immune response to clear malignant tumor cells displaying the same antigen.

Examples of transplant antigens include the CD3 receptor on T cells. Treatment with an antibody to CD3 receptor has been shown to rapidly clear circulating T cells and reverse most rejection episodes.

Examples of autoimmune antigens include IAS chain. Vaccination of mice with an 18 amino acid peptide from IAS chain has been demonstrated to provide protection and treatment to mice with experimental autoimmune encephalomyelitis.

Alternatively, the gene of interest can encode immunoregulatory molecules. These immunoregulatory molecules include, but are not limited to, growth factors, such as M-CSF, GM-CSF; and cytokines, such as IL-2, IL-4, IL-5, IL-6, IL-10, IL-12 or IFN-gamma. Recently, localized delivery of cytokines to tumor tissue has been shown to stimulate potent systemic immunity and enhanced tumor antigen presentation without producing a systemic cytokine toxicity.

Stabilized Plasmid-Based Expression Systems

Bacterial expression systems, by design, typically utilize expression vectors to harness and exploit the protein synthesis machinery of a bacterial host cell to produce a protein of interest. Protein expression levels can often be increased by using high copy number plasmids, or high copy number expression vectors, with the host cells. As discussed above, the introduction of a high copy number expression vector into a bacterial host cell, however, places certain metabolic stresses on the host cell that can cause the host cell to expel the expression vector and thus reduce protein expression levels.

Often overlooked in expression vector engineering is the effect high copy number expression vectors frequently exert on the fitness of the host cell in which the expression vector is introduced. The burden placed upon host bacterial cells carrying multicopy plasmids is the cumulative result of a metabolic cascade. The cascade is triggered by the replication and maintenance of expression vectors (see Bailey, J. E., Host-vector interactions in *Escherichia coli*, p. 29-77. In A. Fiechter (ed.), Advances in Biochemical Engineering. Biotechnology. Springer-Verlag, Berlin (1993), Glick, B. R., Biotechnol. Adv. 13:247-261 (1995), and Smith & Bidochka. Can. J. Microbiol. 44:351-355 (1998)). The cascade is also triggered by transcription and translation of the various expression vector-encoded functions, including the protein of interest. Mechanisms such as those described above explain the observation that plasmid-bearing bacteria grow slower than plasmid-less bacteria. These mechanisms can also explain the observation that growth rate decreases as copy number increases.

Growth rates of recombinant organisms containing expression vectors have been observed to decrease as the expression of a gene of interest increases. The decrease in growth may trigger the induction of various cellular proteases that can degrade the expressed recombinant protein of interest. Reduced growth rate is therefore the inevitable consequence of metabolic burden, which in turn is the cumulative result of a number of physiological perturbations. For example, physiological perturbations result from the expression and accumulation of the protein of interest inside the host bacterium. This accumulation can be harmful to the viability of the host organism and thus a negative selection pressure.

Because metabolic burdens such as those discussed above create a selective pressure for loss of resident expression vectors in the absence of selection, significant loss of expression vectors from the host cell can occur after the host cell has been transformed with the expression vector containing the gene of interest. Spontaneous plasmid loss removes any metabolic burden from the host cell and allow plasmid-less host cell to quickly outgrow the population of plasmid-bearing host cell. The overgrowth of host cells that do not contain and thus do not express the protein of interest reduces overall protein production levels. Therefore, host cells that are not genetically constrained to maintain expression vectors directing the synthesis of high levels of a given protein of interest may produce significantly less protein.

There are a number of means by which this metabolic stress can be reduced. Controlled expression of a protein of interest from multicopy expression vectors represents one solution for synthesis of high levels of protein of interest within host cells. This solution is one embodiment with which to practice the disclosed methods. Utilization of inducible promoters, for example, is one method by which expression from an expression vector can be controlled. Such inducible promoters are discussed in the expression cassette section of this disclosure.

Another embodiment of the methods disclosed herein relates to a plasmid-based expression system engineered to permit the stable expression of high levels of one or more proteins throughout a growing population of cells. Preferably, a stable expression vector is one that perpetuates the expression vector as the host cell replicates. Expression vectors that confer plasmid stability at two independent levels have recently been described in Galen, et al., Immun. 67:6424-6433 (1999) and in U.S. patent application No. 09/204,117, filed Dec. 2, 1998 and Ser. No. 09/453,313, filed Dec. 2, 1999, both of which are hereby incorporated by reference in their entirety.

In this embodiment, partition functions can be incorporated into an expression vector to enhance the inheritance of the plasmid as a given bacterium or host cell grows and subsequently divides. In rare cases where a daughter cell does not inherit at least one copy of the expression vector, a latent post-segregational killing system becomes activated and removes this bacterium or host cell from the growing population through cell lysis.

C. Bacterial Host Cells

A number of species of bacteria are suitable for use with the teachings disclosed herein. Preferably, a suitable bacterial species will be capable of protein export such that the gene of interest can be suitably transcribed such that the protein of interest is translated and exported out of the bacteria. In one embodiment of the invention, the bacteria is administered to an animal, and thus the protein of interest must be exported out of the bacteria into the animal. Invasive and non-invasive bacteria may be used. Examples of some invasive bacteria include, *Shigella* spp., *Listeria* spp., *Rickettsia* spp., and enteroinvasive *Escherichia coli*. A preferred embodiment utilizes *Salmonella* species.

The particular *Salmonella* strain employed with the disclosure below is not critical. Examples of *Salmonella* strains which can be employed in the present invention include *S. Typhi* (ATCC No. 7251) and *S. Typhimurium* (ATCC No. 13311). Attenuated *Salmonella* strains are preferably used in the present invention and include *S. Typhi* aroAaroD (Hone et al, Vacc., 9:810-816 (1991)) and *S. Typhimurium* aroA mutant (Mastroeni et al, Micro. Pathol., 13:477-491 (1992))). Alternatively, new attenuated *Salmonella* strains can be constructed by introducing one or more attenuating mutations as described for *Salmonella* spp. above.

D. Bioreactors

The protein export system described herein is suited for use with bioreactors and similar devices that facilitate the growth of bacteria and the harvesting or use of a desired product or protein of interest. Traditionally there are five stages for recovery of biomolecules from the prior art bioreactors: pre-treatment, solid/liquid separation, concentration, purification, and formulation. There can be a wide range of operations available within each stage. These ranges of operations for each stage are as follows: Pre-treatment: cell disruption, stabilization, sterilization, pasteurization, and flocculation; Solid/liquid Separation: filtration, sedimentation, and centrifugation; Concentration: membranes, precipitation, evaporation, extraction, and freeze concentration; Purification: precipitation, extraction, diafiltration, adsorption, and chromatography; and Formulation: drying, prilling, extrusion, granulation, and tabletting.

In bioreactors where the bacteria do not export the desired product out of the bacteria, one has to scale up the bacteria, induce the bacteria to produce the desired product, and then lyse the bacteria to release the contents. Typically this disruption is performed in the same medium in which the bacteria were grown. One can use a homogenizer or bead mill to mechanically disrupt the bacteria. For non-mechanical disruption, one can use heat shock (which may destroy proteins), detergents, solvents, sequestrants, and enzymes. (Krijgsman, "Releases of Intracellular Components", pp. 27-42, in Product Recovery in Bioprocess Technology, publisher Butterworth-Heinemann Ltd, Oxford, England, 1992)

After the bacteria are disrupted one separates the solid particulates from the fluids (solid/liquid separation). The desired product is usually in the liquid, which one then has to concentrate. Then one extracts the desired product from the concentrated liquid.

Factors which affect separation of the desired product from either the undesired solids or liquids are size, diffusivity, ionic charge, solubility, and density. For size-dependent separation, one can use microfilters, cloth and fiber filters, ultrafiltration, screens/strainers, and gel chromatography. For diffusivity-dependent separation, one can use reverse osmosis and dialysis. Ion exchange chromatography is used for ionic charge-dependent separation. To separate the desired product based on its solubility, one can use solvent extractions. For density-dependent separation, one can use ultracentrifuges, centrifuges, and gravity sedimentation. (Krijgsman, "Downstream Processing in Biotechnology", pp. 2-12, in Product Recovery in Bioprocess Technology, publisher Butterworth-Heinemann Ltd, Oxford, England, 1992).

One advantage of using the disclosed system is that a population of recombinant bacterial host cells can be transformed with an expression vector comprising the disclosed protein export system and that population of bacterial host cells can be maintained in culture and used to produce protein without having to harvest and lyse the bacterial host cells. The culturing of bacterial host cells and the harvesting of the culture medium containing the recombinantly expressed protein of interest can be performed in any type of bioreactor.

There are various types of bioreactors but the family of devices can be divided to two main categories, "free floating" and "bed" bioreactors. In "free floating" bioreactors, the bacteria are floating freely within the media. Examples of "free floating" bioreactors are conventional stirred tank bioreactors, bubble column, airlift loop, multi-purpose tower bioreactors, liquid impelled loop bioreactors, and pumped tower loop bioreactors. An example of the "bed"-type bioreactor is the packed bed bioreactor. In a "bed"-type bioreactor, the bacteria are attached to beads, a membrane, or other solid support. A hybrid type of bioreactor can be produced using a fluidized bed bioreactor where the bacteria are attached to beads or other support but can float in the media. (Mijnbeek, "The Conventional Stirrer Tank Reactor" pp. 39-74; Mijnbeek, "Bubble Column, Airlift Reactors, and Other Reactor Designs" pp. 75-114; Geraats, "An Introduction to Immobilized Systems" pp 115-124; all in "Operational Modes of Bioreactors", publisher Butterworth-Heinemann Ltd, Oxford, England, 1992.)

Using the protein export system described herein with a "bed" bioreactor avoids the step of pre-treatment and solid/liquid separation because the desired protein of interest is exported out of the bacteria into the media. One only needs to remove the media from the bed prior to attempting to isolate the desired product. For "free floating" bioreactors, one can centrifuge the liquid/bacteria mixture to pellet the bacteria. Then one removes the liquid containing the desired protein of interest from the pelleted bacteria. Next one isolates the desired protein of interest from the media. A further benefit of the disclosed system is that the media will contain less undesired proteins than are present in media in which bacteria were disrupted; all the intracellular components of the disrupted bacteria are absent from the media in the present invention. Thus purification of the desired protein of interest is easier. Furthermore, having tags and protease cleavage sites present within the export protein::protein of interest fusion protein further facilitate the isolation and purification of the protein of interest.

One example of a bioreactor is the apparatus taught in U.S. Pat. No. 5,635,368, "Bioreactor with immobilized lactic acid bacteria and the use thereof," to Lommi, et al., Jun. 3, 1997, which is hereby incorporated by reference in its entirety. The Lommi apparatus relates to a bioreactor with immobilized bacteria, which is characterized in that the bacteria are fixed on the surface of a substantially non-compressible carrier. Another example of a bioreactor is found at U.S. Pat. No. 4,910,139, "Method for continuously producing citric acid by dual hollow fiber membrane bioreactor," to Chang, et al., Mar. 20, 1990, which is hereby incorporated by reference in its entirety. This invention relates to growing immobilized bacteria to produce citric acid continuously.

An additional bioreactor apparatus is disclosed in U.S. Pat. No. 5,585,266, "Immobilized cell bioreactor," to Plitt, et al., Dec. 17, 1996, which is hereby incorporated by reference in its entirety. The disclosed Plitt device relates to an immobilized cell bioreactor wherein the cells are harbored within or upon an immobilization matrix including cell support sheets comprised of common textile fabric. U.S. Pat. Nos. 4,665,027 and 5,512,480, both of which are incorporated by reference, disclose other bioreactor embodiments.

E. Vaccines

The protein export system described herein has utility in the production of vaccines. For example, the production of subunit vaccines can be achieved using the protein export system as the system facilitates recombinant protein harvest and reduces the presence of contaminating proteins from the growth medium in which the recombinant host cells are propagated. Recombinant host cells can also be used to generate immunogenic compositions where the recombinant host cell is provided to a subject and the subject's immune system generates an immune response against the proteins exported from the recombinant host cell.

The protein export system described herein can be used with any antigen to prepare a vaccine therefrom, where the antigen is the protein of interest as described above. Vaccine preparation is generally described in New Trends and Developments in Vaccines, edited by Voller et al., University Park Press, Baltimore, Md. U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of antigen in each vaccine dose is selected as an amount which induces an immunoprotective response without significant, adverse side effects in typical vaccinees. Such an amount will vary depending on which specific antigens are employed and the delivery technology used (by way of example only, purified proteins or live bacteria). Generally it is expected that doses comprising purified proteins will comprise 1-1000 µg of total antigen, preferably 2-200 µg. Generally it is expected that doses comprising live bacteria delivering proteins of interest will comprise 1-1000 ng of total antigen of interest. An optimal amount for a particular vaccine can be ascertained by standard studies involving observation of antibody titres and other responses in subjects. Following an initial vaccination, subjects (animal or human) may receive one or more booster doses, for example after 1 and 6 months.

The protein export system can also be used with a live bacterial vector vaccine to increase the efficacy of the preparation. For example, U.S. Pat. No. 5,387,744, to Curtiss et al., entitled "Avirulent microbes and uses therefor: *Salmonella typhi*," which is hereby incorporated by reference, provides for a live bacterial vector vaccine against *S. Typhi*. More specifically, the Curtiss patent provides immunogenic compositions for the immunization of a vertebrate or invertebrate comprising an avirulent derivative of *S. Typhi*. The derivatives having a mutation of the cya and/or crp and/or cdt genes.

The avirulent derivatives taught by Curtiss et al., can be transformed with the protein export system described herein to allow the resulting recombinant organism to act as an immunogenic composition against *S. Typhi*, as well as any other antigen or antigens that are coupled to the protein export protein of the described system.

F. Additional Utility

In addition to therapeutic proteins and antigens which are useful for the pharmaceutical industry, the gene of interest may encode for enzymes, polypeptides, proteins, or amino acids which maybe useful for, by way of example only, the food industry, the nutritional supplement industry, the animal feed industry, the biomediation industry, the waste disposal industry, and the waste treatment industry. For these industries, the protein of interest encoded by the gene of interest may not need to be isolated from the medium of a bioreactor for the protein of interest to serve its function. The protein of interest may be a catalyst for a desired reaction or may act as a precursor component for a desired reaction.

The following examples are provided for illustrative purposes only, and are in no way intended to limit the scope of the present invention.

EXAMPLES

Example 1

Cloning and Mutagenesis of *S. Typhi* clyA

Identification of clyA was accomplished by BLASTN analysis of the recently completed *S. Typhi* genome sequence available from the Sanger Centre (Wellcome Trust Genome Campus, Hinxton, Cambridge, CB10 1SA, UK) (See http://www.sanger.ac.uk/Projects/S_typhi/blast_server.shtml), using the DNA sequence from *E. coli* hlyE (GenBank accession number U57430).

The clyA open reading frame was identified as a 912 bp sequence predicted to encode a 304 residue protein with a molecular mass of 33.8 kDa that is 89.4% identical to *E. coli* HlyE. Although clyA is 85.3% identical to the 915 bp *E. coli* hlyE open reading frame, the upstream transcriptional control region is distantly related with only 33.6% identical bases within a 250 bp region.

Based on this analysis, primers were designed for PCR amplification of a promoterless genetic cassette encoding ClyA in which an optimized ribosome-binding site was engineered 5'-proximal to the ATG start codon. The primer sequences are listed in Table 1.

TABLE 1

Primers used in construction and sequence analysis of the plasmid cassettes

| Primer Number | Sequence[a] | Cassette created | Template |
|---|---|---|---|
| 1 | 5'GGATCCAAAATA*AGGAGGAAAAAAAAATG*ACTAGTATTT TTGCAGAACAAACTGTAGAGGTAGTTAAAAGCGCGATCGA AACCGC AGATGGGGCATTAGATC-3' (SEQ ID NO: 3) | clyA-tetA | CVD 908-htrA |
| 2 | 5'CCTAGGTTATCAGCTAGCGACGTCAGGAACCTCGAAAAG CGTCTTCTTACCATGACGTTGTTGGTATTCATTACAGGTGTT AATCAT TTTCTTTGCAGCTC-3' (SEQ ID NO: 4) | " | " |
| 3 | 5'CACGGTAAGAAGACGCTTTTCGAGGTTCCTGACGTCGCTA GCTGATAACCTAGGTCATGTTAGACAGCTTATCATCGATA AGCTTT AATGCGGTAGT-3' (SEQ ID NO: 5) | " | pBR322 |
| 4 | 5'AGATCTACTAGTGTCGACGCTAGCTATCAGGTCGAGGTG GCCCGGCTCCATGCACCGCGACGCAACGCG-3' (SEQ ID NO: 6) | " | " |
| 5 | 5'ACTAGTCACCCAGAAACGCTGGTGAAAGTAAAAGATGCT GAA GATCAGTTGGGTGCACGA-3' (SEQ ID NO: 7) | bla-tetA | pGEM-T |
| 6 | 5'CATTAAAGGTTATCGATGATAAGCTGTCAAACATGAGCT AGCCTAGGTCATTACCAATGCTTAATCAGTGAGGCACCTAT CTCAGC GATCTGTCTATTTCG-3' (SEQ ID NO: 8) | " | " |
| 7 | 5'CGAAATAGACAGATCGCTGAGATAGGTGCCTCACTGATTA AGCATTGGTAATGACCTAGGCTAGCTCATGTTTGACAGCT TATCAT CGATAACCTTTAATG-3' (SEQ ID NO: 9) | " | pBR322 |
| 8 | 5'GCGCACTAGTAAAGAAACGAACCAAAAGCCATATAAGG AAA CATACGGCATTTCCCATATTACACGCCATG-3' (SEQ ID NO: 10) | sacB-tetA | pIB279 |
| 9 | 5'TAAACTACCGCATTAAAGCTTATCGATGATAAGCTGTCAA ACATGACCCGGGTCACTATTTGTTAACTGTTAATTGTCCTT GTTCAA GGATGCTGTCTTTGAC-3' (SEQ ID NO: 11) | " | " |
| 10 | 5'TCATGTTTGACAGCTTATCATCGATAAGCTTTAATGCGGT AGT TTA-3' (SEQ ID NO: 12) | " | pBR322 |
| 11 | 5'GCGCAGATCTTAATCATCCAC*AGGAGGC*GCTAGC*ATG*AG TAAAGGAGAAGAACTTTTCACTGGAGTTGTCCCAATTCTTG-3' (SEQ ID NO: 13) | gfpuv-tetA | pGEN84 |
| 12 | 5'GTGATAAACTACCGCATTAAAGCTTATCGATGATAAGCTG TCAAACATGAGCGCTCTAGAACTAGTTCATTATTTGTAGA GCTCATCCATGCCATGTGTAATCCCAGCAG-3' (SEQ ID NO: 14) | " | " |

[a]Relevant restriction sites are designated in bold case, underlined; ribosome binding sites and start codons are designated in italics.

Relevant restiction sites are designated in bold case, underlined; ribsome binding sites and start codons are deignated in italics.

To facilitate recovery, overlapping PCR techniques were used to create a promoterless 2252 base pair clyA-tetA genetic cassette synthesized by overlapping PCR as previously described using primers 1 and 2 with chromosomal template DNA from CVD 908-htrA, and primers 3 and 4 with template derived from pBR322, and recovered in pGEM-T (Promega, Madison Wis.) transformed into E. coli DH5α.

Recombinant clones were screened on solid agar medium containing sheep red blood cells. Specifically, screening for hemolytic activity was performed on freshly prepared 1XLB agar medium containing appropriate antibiotic selection and 5% sheep blood. Plates were then incubated at 37° C. for 24 hours to detect zones of red blood cell (RBC) hemolysis. Several colonies were immediately identified which produced clear halos of hemolysis. This observation suggested that if clyA requires accessory proteins for translocation out of the bacterium, these proteins are apparently common to both S. Typhi and E. coli. A positive isolate, designated pGEM-TclyA, was chosen for further use.

The functional roles of various regions of ClyA were examined to provide information for the proper engineering of recombinant fusion proteins encoding an antigen fused to ClyA. Specifically, the role played by the amino terminus, the carboxyl terminus, or both, in exportation of hemolysin out of the bacterium was examined.

To accomplish this, clyA was randomly mutagenize using the transposon TnphoA. The "phoa" of "TnphoA" encodes alkaline phosphatase (See Manoil & Bechwith, PNAS Vol 82, pp 8129-8133, 1985). Transposition of TnphoA allows for random formation of in-frame fusions of the N-terminus of PhoA onto a given target protein. TnphoA mutagenesis was carried out after electroporation of pGEM-TclyA, expressing functional S. Typhi ClyA hemolysin, into DH5α to yield DH5α (pGEM-TclyA). A cross-streak mating was then performed between DH5α (pGEM-TclyA) and the TnphoA donor strain SM10(pRT733) and selecting transconjugants on 2XLB50 supplemented with tetracycline, carbenicillin, and kanamycin at 10 µg/ml, 50 µg/ml, and 10 µg/ml respectively (2XLB50+T10C50K10). Bacteria were then pooled and grown up in broth cultures for plasmid purification, and purified plasmids retransformed into the phoAΔ20 mutant E. coli strain CC118 for selection of Pho⁺ transformants on 2XLB50+T10C50K10 supplemented with 200 µg/ml of the alkaline phosphatase substrate 5-Bromo-4-Chloro-3-Indolyl-Phosphate (BCIP; Sigma, St. Louis, Mo.). Target protein fusions that are N-terminally secreted into the periplasm, surface exposed, or exported out of the bacterium entirely, can easily be screened using the chromogenic substrate BCIP to detect deep blue halos of hydrolysis; proteins which are C-terminally secreted will not be detected using this method.

Using TnphoA mutagenesis, 4 of 621 PhoA⁺ colonies were identified that no longer displayed hemolytic activity. Sequencing of one isolate confirmed the in-frame insertion of PhoA after residue 179 (Ala) of ClyA. This insertion truncated ClyA in the proposed hydrophobic transmembrane region and removes the remaining 125 carboxyl-terminal residues. It was therefore concluded that the carboxyl-terminus of S. Typhi ClyA is not required for transport of the cytoplasm of E. coli (and presumably from S. Typhi also), and that genetic fusion of heterologous genes potentially encoding exported protein fusions should be carried out at the 3'-terminus of clyA.

Example 2

Construction of Carboxyl-Terminal Fusions of Test Antigens to ClyA

To test the ability to export passenger proteins fused at the carboxyl terminus of ClyA, the bla gene encoding the RTEM-1 β-lactamase protein which confers resistance to both ampicillin and carbenicillin, was chosen for experimentation.

This protein fusion was engineered as a genetic fusion of a SpeI cassette inserted in-frame into the NheI site adjacent to the tandem stop codons at the clyA 3'-terminus of pSEC84. Initially, an 807 bp SpeI-NheI fragment encoding the mature 268 amino acid β-lactamase without the 23 residue signal sequence was synthesized from a pBR322 derivative by PCR. The purified fragment was then inserted in-frame into the engineered carboxyl terminal NheI site of clyA to create a 1742 bp clyA-bla genetic fusion encoding a predicted 62.9 kDa fusion protein. The desired plasmid construct was easily recovered in isolated colonies from cultures grown in the presence of 5 µg/ml carbenicillin, but plasmids recovered after selection with 50 µg/ml carbenicillin appeared to be unstable and genetically rearranged.

bla-tetA Fusion

Because of the problem with plasmid stability and genetic rearrangement of the clyA-bla construct described above, the bla-tetA fusion was synthesized as a 2111 bp SpeI cassette by overlapping PCR using primers 5 and 6 with pGEM-T template and primers 7 and 4 with template derived from pBR322; insertion of this cassette into pSEC84 cleaved with NheI yielded pSEC84bla (see FIG. 1B).

After introduction into CVD 908-htrA, colonies were screened for retention of hemolytic activity, and then screened for β-lactamase activity using the chromogenic substrate nitrocefin at a concentration of 100 µg/ml in 2XLA50+DHB+T10; plates were incubated at 30° C. for at least 16 hours and examined for the presence of red halos around colonies indicating cleavage of nitrocefin. Red halos were observed around CVD 908-htrA(pSEC84bla), indicating cleavage of nitrocefin, confirmed the presence of enzymatically active β-lactamase. It was concluded that an approximate doubling of the molecular mass of ClyA from 34 kDa to 63 kDa resulted in a 2 domain fusion protein in which both domains apparently folded correctly to maintain the expected biological activity of each domain.

sacB-tetA Fusion

To investigate the versatility of ClyA as a fusion partner to export heterologous antigens out of S. Typhi, the efficiency of ClyA to export the potentially lethal levansucrase encoded by sacB from Bacillus subtilis was examined. Expression of the sacB gene is lethal when expressed within the cytoplasm of enteric bacteria, including S. Typhi, growing in the presence of sucrose. Construction of a ClyA-SacB protein fusion with a predicted molecular mass of 83.9 kDa, for introduction into CVD 908-htrA was attempted. This fusion was engineered as a sacB-tetA SpeI cassette encoding the mature 445 residue 50.0 kDa levansucrase, without the 29 amino acid signal sequence, and inserted in-frame into the engineered carboxyl terminal NheI site of ClyA in pSEC84. CVD 908-htrA carrying the desired construct was selected using tetracycline and screened in the presence of sucrose for survival. If ClyA-SacB failed to be exported out of the cytoplasm, no isolates would be recovered, but for fusions either surface expressed or fully exported out of the bacterium into the surrounding medium, an enzymatically active SacB moiety would be expected to cleave sucrose to release glucose, which would immediately be transported into the bacterium and metabolized.

The sacB-tetA cassette was synthesized using primers 8 and 9 with pIB279 template and primers 10 and 4 as above to create a 2653 bp SpeI cassette inserted into pSEC84 generating the clyA::sacB fusion of pSEC84sacB (SEQ ID NO:18) (see FIG. 1C). After introduction into CVD 908-htrA, colonies were again screened for retention of hemolytic activity, and then examined for levansucrase activity by plating on MacConkey agar base medium (Difco) supplemented with DHB and either sucrose (8% or 16% w/v) or 8% sucrose+8% arabinose as the sole carbohydrate source. Plates were incubated at 30° C. for 16-24 hours to recover isolated cfus and determine fermentation of the carbohydrate; additional incubation at room temperature for several more days was required to observe formation of the polysaccharide-like domes over colonies.

As shown in FIGS. 2B and 2D, growth of CVD 908-htrA (pSEC84sacB) was excellent when grown on indicator medium containing either 8% sucrose or 16% sucrose as the sole carbohydrate source (where grown on MacConkey agar base medium). Indeed, a polysaccharide-like dome was observed to form over isolated CVD 908-htrA(pSEC84sacB) colonies which was not observed for CVD 908-htrA (FIGS. 2A and 2C), and intensified with increasing concentration of sucrose. Hypothesizing that this polysaccharide-like material was levan, formed by the levansucrase-catalyzed polymerization of fructose liberated from hydrolysis of sucrose, we attempted to block this polymerization by introducing 8% L-arabinose which is known to inhibit levansucrase. As shown in FIG. 2F, domes were no longer observed, with CVD 908-htrA and CVD 908-htrA(pSEC84sacB) colonies now appearing similar.

Figure 3:
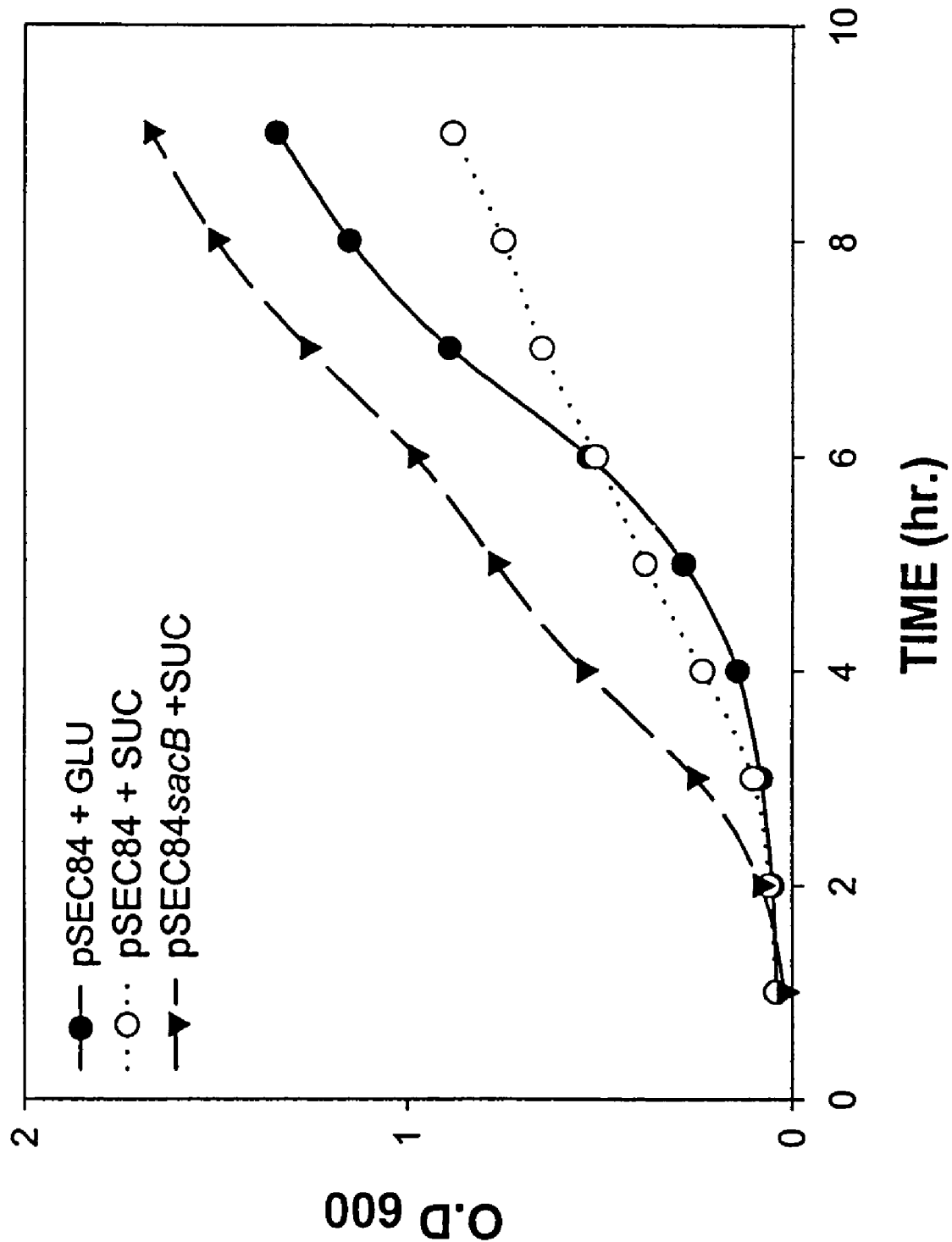
FIG. 3 illustrates the growth of CVD 908-htrA expressing either ClyA (pSEC84) or ClyA-SacB (pSEC84sacB), grown in 2XLB50 broth supplemented with DHB and either 10% sucrose or 10% glucose.

If ClyA-SacB protein fusions are indeed exported out of CVD 908-htrA(pSEC84sacB), then cleavage of sucrose by the SacB domain to liberate free glucose should provide a metabolic advantage compared CVD 908-htrA when these strains are grown as broth cultures in the presence of sucrose. To test this hypothesis, 100 ml broth cultures of either CVD 908-htrA(pSEC84) or CVD 908-htrA(pSEC84sacB) were set up in 1 liter baffle flasks containing 2XLB50+DHB+K10 plus 10% sucrose and growth was compared to CVD 908-htrA(pSEC84) cultures grown in the presence of 10% glucose as a positive control. As shown in FIG. 3, CVD 908-htrA (pSEC84sacB) was observed to grow faster in the presence of sucrose than either CVD 908-htrA(pSEC84) growing with glucose or sucrose, an observation confirmed with viable counts. When taken together with results observed above for ClyA-Bla, the data strongly suggest that ClyA is a versatile fusion partner for export out of out of bacteria properly folded fusion proteins in which the biological activity of the fused domains is preserved.

clyA::gfpuv Fusion

Figure 4:
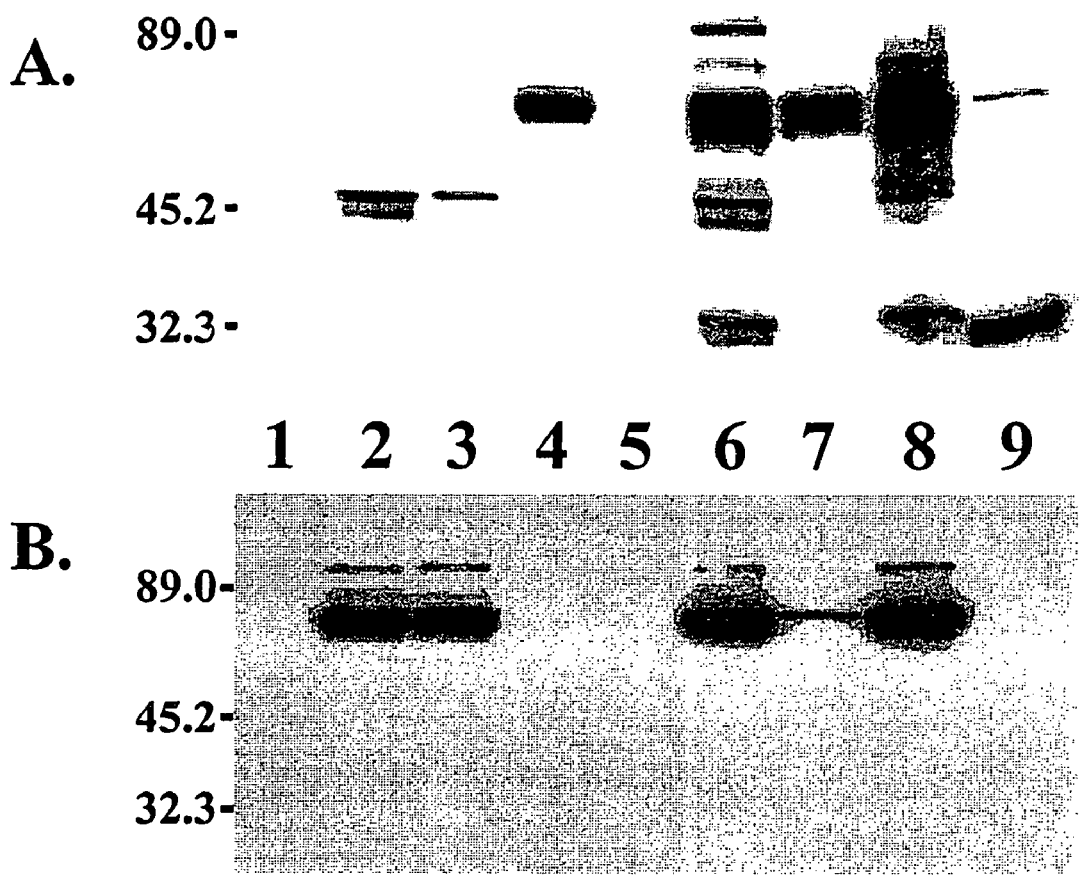
FIG. 4 illustrates Western immunoblot analysis of bacterial cell fractions from either CVD 908-htrA (lanes 1-3) or CVD 908-htrA(pSEC84gfpuv) (lanes 4-8). Cell fractions are loaded as follows: supernatants, lanes 1 and 4; cytoplasmic, lanes 2 and 6; periplasmic, lane 5; insoluble, lane 7; whole cell, lanes 3 and 8; and 50 ng GFPuv, lane 9. Membranes with identical samples were probed with antibodies specific for GFPuv (panel A) or *E. coli* GroEL (panel B).

To further define the export properties of ClyA and specifically verify the presence of ClyA fusion products in the supernatant of exponentially growing CVD 908-htrA, a genetic fusion of clyA was constructed where clyA was fused to the fluorescent reporter green fluorescent protein (GFPuv) creating the clyA::gfpuv cassette of pSEC84gfpuv (see FIG. 1D), and isogenic to both pSEC84bla and pSEC84sacB. Again, CVD 908-htrA(pSEC84gfpuv) remained hemolytic but with reduced fluorescence when compared to cytoplasmically expressed GFPuv. Using GFP polyclonal antibody (BD Biosciences Clontech, Palo Alto, Calif.), the export of ClyA-GFPuv into the culture supernatant was examined using Western immunoblot analysis, as shown in FIG. 4. FIG. 4 illustrates a set of Western immunoblots analyzing bacterial cell fractions from either CVD 908-htrA (lanes 1-3) or CVD 908-htrA(pSEC84gfpuv) (lanes 4-8). Cell fractions are loaded as follows: supernatants, lanes 1 and 4; cytoplasmic, lanes 2 and 6; periplasmic, lane 5; insoluble, lane 7; whole cell, lanes 3 and 8; and 50 ng GFPuv, lane 9. Membranes with identical samples were probed with antibodies specific for GFPuv (panel A) or E. coli GroEL (panel B). As can be seen in this figure, a significant amount of the expected 61 kDa protein fusion is detected in 0.5 ml of TCA-precipitated supernatant from CVD 908-htrA(pSEC84gfpuv) (lane 4); an irrelevant cross-reacting species of approximately 45 kDa is also detected in the cytoplasm of CVD 908-htrA (lane 2) and in the cytoplasmic, insoluble, and whole cell fractions of CVD 908-htrA(pSEC84gfpuv); interestingly, lane 5 suggests that very little ClyA-GFPuv is recovered from the periplasmic space.

Conclusion

The results from this work clearly support the conclusion that the cryptic hemolysin ClyA from S. Typhi can be used to facilitate the export of heterologous antigen domains out of the attenuated vaccine strain CVD 908-htrA and into the surrounding medium. Furthermore this work demonstrates that ClyA can be used to facilitate the export of a fusion protein out of bacteria into the surrounding medium. As illustrated above, the ability to export properly folded proteins of interest fused at the carboxyl terminus of ClyA was shown using the bla gene encoding the RTEM-1 β-lactamase protein which confers resistance to both ampicillin and carbenicillin. The bla gene of pBR322 is 861 bp in length and encodes a 31.5 kDa protein with a 23 amino acid signal sequence directing N-terminal secretion of β-lactamase into the periplasmic space. The work above indicates the successful engineering of a gene fusion encoding a functional ClyA-β-lactamase protein fusion which retained both hemolytic activity and the ability to cleave the chromogenic β-lactamase substrate nitrocefin to produce red halos against a yellow background of uncleaved nitrocefin.

Interestingly, attempts to select for such expression vectors when growing transformants in rich medium supplemented with 50 µg/ml of either carbenicillin or ampicillin were unsuccessful and only extensively rearranged plasmids were recovered as judged by restriction mapping. It has been conclusively demonstrated that cytoplasmically expressed β-lactamase confers resistance to ~5 µg/ml of ampicillin, while appropriately expressed periplasmic β-lactamase confers resistance to >4000 µg/ml of ampicillin. However, surface display of β-lactamase protein fusions have been shown to confer resistance to ~100 µg/ml of ampicillin. Indeed, Chervaux et al. have reported that HlyA-mediated secretion of β-lactamase fusions out of E. coli again confer low-level resistance to ~5 µg/ml of ampicillin. They demonstrated that even though the specific activity of the intact P-lactamase domain of the surface fusion remained similar to that of unmodified β-lactamase, resistance to high levels of ampicillin was not observed, and they concluded that bacterial resistance to β-lactam antibiotics requires significant concentrations of β-lactamase within the periplasmic space close to the killing targets. Based on such observations, it was concluded that properly folded ClyA-β-lactamase protein fusions were synthesized within CVD 908-htrA(pSEC84bla) and exported to confer a hemolytic phenotype, as well as β-lactamase-mediated hydrolysis of the chromogenic cephalosporin nitrocefin, without conferring resistance to ampicillin or carbenicillin.

To more clearly define the nature of ClyA-mediated export of heterologous antigen domains out of CVD 908-htrA, and perhaps rule out the involvement of periplasmic intermediates, fusions of sacB, encoding the potentially lethal levansucrase from *B. subtilis* were studied. Levansucrase is a 50 kDa single polypeptide exoenzyme that catalyzes the hydrolysis of sucrose to yield free glucose and fructose, and in turn catalyzes the polymerization of fructose into long polymers called levan. Secretion of levansucrase from *B. subtilis* growing on medium containing sucrose results in the growth of isolated colonies covered by an impressive dome of viscous levan after extended incubation at room temperature.

It is well established that cytoplasmic and periplasmic expression of levansucrase encoded by sacB is lethal for a variety of bacteria growing in the presence of sucrose. It has recently been shown using signal peptide mutations that levansucrase becomes lethal within the cytoplasm of *B. subtilis* grown in the presence of sucrose, and that inactivation of the fructose polymerase activity was essential for removal of sucrose-induced lethality. It was therefore reasoned that failure of ClyA-SacB fusions to be exported out of both the cytoplasm and periplasmic space of CVD 908-htrA should result in significant intracellular accumulation of the fusion protein resulting in lethality for CVD 908-htrA (pSEC84sacB) growing in the presence of sucrose.

As shown in FIG. 2B, however, CVD 908-htrA (pSEC84sacB) was observed not only to grow in the presence of 8% sucrose but to ferment the sugar, a phenotype not observed for CVD 908-htrA(pSEC84) grown under the identical conditions. As the concentration of sucrose was increased from 8% to 16% sucrose, fermentation of sucrose also increased with the accumulation of impressive domes of levan-like material which vanished in the presence of the levansucrase inhibitor arabinose. Similar observations of levansucrase activity were reported by Jung et al. for a surface expressed levansucrase domain fused to the carboxyl terminus of the ice nucleation protein of *Pseudomonas syringae* and expressed within *E. coli*. In view of these results, it was concluded that the engineered CVD 908-htrA(pSEC84sacB) had the ability to utilize sucrose as a carbon source in broth culture experiments in which CVD 908-htrA(pSEC84sacB) was observed to grow faster than CVD 908-htrA(pSEC84) grown either in the presence of sucrose or pure glucose. It was again concluded that, as with the ClyA-β-lactamase protein fusions described above, that properly folded ClyA-SacB protein fusions were synthesized within CVD 908-htrA, and exported to confer both the expected hemolytic phenotype, as well as levansucrase activity allowing for the extracellular catabolism of an alternate carbohydrate source not utilized by the plasmid-less host strain.

Example 3

Bioreactor Protein Expression of a ClyA-SacB Fusion

A bioreactor is prepared according to the teachings of U.S. Pat. No. 5,635,368, which is hereby incorporated by reference in its entirety. Briefly, granular derivatized cellulose is manufactured according to U.S. Pat. No. 4,355,117 as follows: 25 parts of fibrous cellulose is mixed with 25 parts of titanium dioxide and the mixture is compounded with 50 parts of high-impact polystyrene using a twin-screw extruder. The extrudate is cooled in water, and sieved to a particle size of 0.35-0.85 mm. The sieved granular agglomerated cellulose particles are derivatized to form DEAE cellulose as described in the U.S. Patent above.

Next, ten (10) grams of the granular DEAE-cellulose is reduced to a slurry in distilled water and soaked for 5 hours with occasional stirring. The hydrated carrier is then decanted with the distilled water and transferred into a glass column with an inner diameter of 15 mm where it forms a bed with a height of 145 mm.

Bacteria transformed with pSEC84sacB (see Example 2) are cultured for 48 hours at 30° C. Fifty (50) milliliters of the cell suspension is pumped through the carrier bed at a flow velocity of 25 ml/hour. Subsequently, additional amounts of culture medium is pumped through the carrier bed. The outflow of the column is collected and the recombinantly expressed ClyA-SacB fusion protein (encoded by SEQ ID NO: 19) is isolated and purified from the outflow. Cleavage of SacB would provide ample commercial amounts of levansucrase for the generation of levan.

Example 4

His-Tag Protein Purification Under Denaturing Conditions

A bacterial culture is transformed with an expression vector containing an expression cassette comprising the coding sequence for an attenuated ClyA protein fused to a sacB gene, which is fused to a coding sequence encoding a protease recognition site, which is fused to a polyhistidine tag encoding sequence. The bacterial culture is introduced into a bioreactor such as that described in Example 3.

The culture is placed under conditions promoting expression of the recombinant fusion protein, which is exported into the culture medium. The culture medium is collected and applied to a Ni column (HISTRAP; Pharmacia) equilibrated with a urea containing buffer at a concentration sufficiently high to denature the protein. The column is then washed and eluted. The eluate is analyzed by gel electrophoresis to determine the presence of the purified protein.

Purified protein containing fractions are dialyzed against an enzyme digestion buffer. The dialyzed samples are then pooled and subjected proteolysis catalyzed by the appropriate enzyme. The proteolyzed sample is purified to eliminate the deleted polyhistidine tag, leaving the isolated, purified protein.

Example 5

Construction of Attenuated CVD 908-htrA that Expresses Frag C and Raising an Immune Response Thereto A ClyA-Frag C fusion protein is generated in CVD 908-htrA according to the steps discussed in Example 1. Our approach is to express a codon-optimized toxC open reading frame encoding fragment C of tetanus toxin inserted into ClyA expressed from the expression vector disclosed herein. Export of fragment C is accomplished through an in-frame genetic fusion of toxC to the 3' terminus of clyA and carried on the oriE1 replicon pSEC84 as a 1426 bp $P_{ompC}$-clyA EcoRI-NheI cassette. toxC encoding fragment C is re-engineered from prior art constructs using the forward primer 5'-GCGCACTAGTAAAAACCTTGATTGT-TGGGTCGACAACGAAGAAGACATCGATGTT-A TCCTGAAAAAGTCTACCATTCTGAACT-TGGACATCAAC-3' (SEQ ID NO: 15) and the reverse primer 5'-AACTACCGCATTAAAGCTTATCGAT-GATAAGCTGTCAAACATGAGCTAGCCTAGGT CATT-AGT-CGTTGGTCCAACCTTCATCGGTCGGAAC- GAAGTA-3' (SEQ ID NO: 16) to generate the desired PCR product (1424 bp). The toxC cassette is then subcloned into pSEC84 digested with NheI to construct pSEC84toxC. The DNA sequence of the intended clyA-toxC fusion junction is confirmed using the sequencing primer 5'-CGATGCG-GCAAAATTGAAATTAGCCACTGA-3' (SEQ ID NO: 17) which hybridizes 172 bases upstream of the engineered NheI site at the 3'-terminus of clyA. Constructs are screened for retention of hemolytic activity and confirmed for export of the ClyA-Frag C into the supernatant by Western immunoblot analysis.

Groups often 6 weeks old Balb/c mice are immunized intranasally with $1.0 \times 10^{10}$ cfu of strain CVD 908-htrA expressing the ClyA-Frag C fusion protein. Mice are bled prior and 30 days after their immunization, and their serum is stored at $-20°$ C. until use. Antibodies present in the serum against ClyA and Frag C antigens are determined by ELISA. The results indicate that immunization with strain CVD 908-htrA expressing the ClyA-Frag C fusion protein elicits antibody levels against the Frag C antigen that are significantly higher than those obtained with strain 908-htrA not expressing the ClyA-Frag C fusion protein. The results demonstrate that the expression of the Frag C antigen as a fusion protein with ClyA enhances the immune response against this antigen. Protective immunity against tetanus toxin is confirmed by challenging immunized mice with otherwise lethal doses of natural tetanus toxin.

While the disclosure above describes the invention in detail and with reference to specific embodiments thereof, it will be apparent to one of ordinary skill in the art that various changes and modifications can be made therein without departing from the spirit and scope thereof.

REFERENCES

Atkins, A., N. R. Wyborn, A. J. Wallace, T. J. Stillman, L. K. Black, A. B. Fielding, M. Hisakado, P. J. Artymiuk, and J. Green. 2000. Structure-function relationships of a novel bacterial toxin, hemolysin E. The role of $\alpha_G$. J. Biol. Chem. b:41150-41155.

Bailey, J. E., Host-vector interactions in *Escherichia coli*, p.29-77. In A. Fiechter (ed.), Advances in Biochemical Engineering. Biotechnology. Springer-Verlag, Berlin (1993).

Balbas, P., X. Soberon, E. Merino, M. Zurita, H. Lomeli, F. Valle, N. Flores, and F. Bolivar. 1986. Plasmid vector pBR322 and its special-purpose derivatives-a review. Gene 50:3-40.

Blomfield, I. C., V. Vaughn, R. F. Rest, and B. I. Eisenstein. 1991. Allelic exchange in *Escherichia coli* using the *Bacillus subtilis* sacB gene and a temperature-sensitive pSC101 replicon. Mol. Microbiol. 5:1447-1457.

Boe, L., K. Gerdes, and S. Molin. 1987. Effects of genes exerting growth inhibition and plasmid stability on plasmid maintenance. J. Bacteriol. 169:4646-4650.

Borchert, T. V. and V. Nagarajan. 1991. Effect of signal sequence alterations on the export of levansucrase in *Bacillus subtilis*. J. Bacteriol. 173:276-282.

Bramucci, M. G. and V. Nagarajan. 1996. Direct selection of cloned DNA in *Bacillus subtilis* based on sucrose-induced lethality. Appl. Environ. Microbiol. 62:3948-3953.

Chervaux, C., N. Sauvonnet, A. Le Clainche, B. Kenny, A. L. Hunt, J. K. Broome-Smith, and I. B. Holland. 1995. Secretion of active β-lactamase to the medium mediated by the *Escherichia coli* haemolysin transport pathway. Mol. Gen. Genet. 249:237-245.

Corchero, J. L. and A. Villaverde. 1998. Plasmid maintenance in *Escherichia coli* recombinant cultures is dramatically, steadily, and specifically influenced by features of the encoded proteins. Biotechnol. Bioeng. 58:625-632.

Cserjan-Puschmann, M., W. Kramer, E. Duerrschmid, G. Streidner, and K. Bayer. 1999. Metabolic approaches for the optimisation of recombinant fermentation processes. Appl. Microbiol. Biotechnol. 53:43-50.

Datta, N. and P. Kontomichalou. 1965. Penicillinase synthesis controlled by infectious R factors in Enterobacteriaceae. Nature 208:239-241.

Dedonder, R. 1966. Levansucrase from *Bacillus subtilis*, p. 500-505. In E. F. Neufeld and V. Ginsburg (eds.), Methods in Enzymology. Academic Press, New York.

del Castillo, F. J., S. C. Leal, F. Moreno, and I. del Castillo. 1997. The *Escherichia coli* K-12 sheA gene encodes a 34-kDa secreted haemolysin. Mol. Microbiol. 25:107-115.

Fouet, A., M. Arnaud, A. Kier, and G. Rapoport. 1984. Characterization of the precursor form of the exocellular levansucrase from *Bacillus subtilis*. Biochem. Biophys. Res. Commun. 119:795-800.

Galen, J. E., O. G. Gomez-Duarte, G. Losonsky, J. L. Halpern, C. S. Lauderbaugh, S. Kaintuck, M. K. Reymann, and M. M. Levine. 1997. A murine model of intranasal immunization to assess the immunogenicity of attenuated *Salmonella typhi* live vector vaccines in stimulating serum antibody responses to expressed foreign antigens. Vaccine 15:700-708.

Galen, J. E. and M. M. Levine. 2001. Can a 'flawless' live vector vaccine strain be engineered? Trends in Microbiology 9:372-376.

Galen, J. E., J. Nair, J. Y. Wang, S. S. Wasserman, M. K Tanner, M. Sztein, and M. M. Levine. 1999. Optimization of plasmid maintenance in the attenuated live vector vaccine strain *Salmonella typhi* CVD 908-htrA. Infect. Immun. 67:6424-6433.

Gay, P., D. Le Coq, M. Steinmetz, T. Berkelman, and C. I. Kado. 1985. Positive selection procedure for entrapment of insertion sequence elements in Gram-negative bacteria. J. Bacteriol. 164:918-921.

Gay, P., D. Le Coq, M. Steinmetz, E. Ferrari, and J. A. Hoch. 1983. Cloning structural gene sacB, which codes for exoenzyme levansucrase of *Bacillus subtilis*: expression of the gene in *Escherichia coli*. J. Bacteriol. 153:1424-1431.

Glick, B. R., Biotechnol. Adv. 13:247-261 (1995).

Han, Y. W. 1990. Microbial levan. Advances in Applied Microbiology 35:171-194.

Harcum and Bentley. 1993. Biotechnol. Bioeng. 42:675-685.

Hone, D. M., A. M. Harris, S. Chatfield, G. Dougan, and M. M. Levine. 1991. Construction of genetically defined double aro mutants of *Salmonella typhi*. Vaccine 9:810-816.

Jung, H., J. Lebeault, and J. Pan. 1998. Surface display of *Zymomonas mobilis* levansucrase by using the ice-nucleation protein of *Pseudomonas syringae*. Nat. Biotechnol. 16:576-580.

Lattemann, C. T., J. Maurer, E. Gerland, and T. F. Meyer. 2000. Autodisplay: functional display of active β-lactamase on the surface of *Escherichia coli* by the AIDA-I autotransporter. J. Bacteriol. 182:3726-3733.

Le Coq, D., P. Ratet, M. Steinmetz, and P. Gay. 1984. A genetic approach to levansucrase secretion in *Bacillus subtilis*, p. 141-152. In A. T. Ganesan and J. A. Hoch (eds.), Genetics and biotechnology of bacilli. Academic Press, New York.

LeBrun, E. and R. van Rapenbusch. 1980. The structure of *Bacillus subtilis* levansucrase at 3.8 A resolution. J. Biol. Chem. 255:12034-12036.

Ludwig, A., S. Bauer, R. Benz, B. Bergmann, and W. Goebel. 1999. Analysis of the SlyA-controlled expression, subcellular localization and pore-forming activity of a 34 kDa haemolysin (ClyA) from *Escherichia coli* K-12. Mol. Microbiol. 31:557-567.

Matthew, M. and R. W. Hedges. 1976. Analytical isoelectric focusing of R factor-determined β-lactamases: correlation with plasmid compatibility. J. Bacteriol. 125:713-718.

McDermott, P. J., P. Gowland, and P. C. Gowland. 1993. Adaptation of *Escherichia coli* growth rates to the presence of pBR322. Lett. Appl. Microbiol. 17:139-143.

Orr, N., J. E. Galen, and M. M. Levine. 1999. Expression and immunogenicity of a mutant diphtheria toxin molecule, $CRM_{197}$, and its fragments in *Salmonella typhi* vaccine strain CVD 908-htrA. Infect. Immun. 67:4290-4294.

Oscarsson, J., Y. Mizunoe, L. Li, X. Lai, A. Wieslander, and B. E. Uhlin. 1999. Molecular analysis of the cytolytic protein ClyA (SheA) from *Escherichia coli*. Mol. Microbiol. 32:1226-1238.

Oscarsson, J., Y. Mizunoe, B. E. Uhlin, and D. J. Haydon. 1996. Induction of haemolytic activity in *Escherichia coli* by the slyA gene product. Mol. Microbiol. 20:191-199.

Pecota, D. C., C. S. Kim, K Wu, K. Gerdes, and T. K. Wood. 1997. Combining the hok/sok, parDE, and pnd postsegregational killer loci to enhance plasmid stability. Appl. Environ. Microbiol. 63:1917-1924.

Pluckthun, A. and J. R. Knowles. 1987. The consequences of stepwise deletions from the signal-processing site of β-lactamase. J. Biol. Chem. 262:3951-3957.

Ried, J. and A. Collmer. 1987. An npI-sacB-sacR cartridge for constructing directed,unmarked mutations in Gram-negative bacteria by marker exchange-eviction mutagenesis. Gene 57:239-246.

Sambrook, J., E. F. Fritsch, and T. Maniatis. 1989. AnonymousMolecular cloning: a laboratory manual. Cold Spring Harbor Laboratory Press, Cold Spring Harbor, N.Y.

Sambrook, J. and D. W. Russell. 2001. Expression of cloned genes in *Escherichia coli*, p. 15.35AnonymousMolecular cloning. A laboratory manual. Cold Spring Harbor Laboratory Press, Cold Spring Harbor.

Shaw, K. J., P. N. Rather, R. S. Hare, and G. H. Miller. 1993. Molecular genetics of aminoglycoside resistance genes and familial relationships of the aminoglycoside-modifying enzymes. Microbiol. Rev. 57:138-163.

Smith & Bidochka. Can. J. Microbiol. 44:351-355 (1998).

Steinmetz, M., D. Le Coq, H. B. Djemia, and P. Gay. 1983. Genetic analysis of sacB, the structural gene of a secreted enzyme, levansucrase of *Bacillus subtilis* Marburg. Mol. Gen. Genet. 191:138-144.

Summers, D. K. 1998. Timing, self-control and sense of direction are the secrets of multicopy plasmid stability. Mol. Microbiol. 29:1137-1145.

Sutcliffe, J. G. 1978. Nucleotide sequence of the ampicillin resistance gene of *Escherichia coli* plasmid pBR322. Proceedings of the National Academy of Sciences USA 75:3737-3741.

Tacket, C. O., M. Sztein, G. Losonsky, S. S. Wasserman, J. P. Nataro, R. Edelman, D. Pickard, G. Dougan, S. Chatfield, and M. M. Levine. 1997. Safety of live oral *Salmonella typhi* vaccine strains with deletions in htrA and aroC aroD and immune responses in humans. Infect. Immun. 65:452-456.

Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.

Wang, J. Y., F. Noriega, J. E. Galen, E. M. Barry, and M. M. Levine. 2000. Constititive expression of the Vi polysaccharide capsular antigen in attenuated *Salmonella enterica* serovar Typhi oral vaccine strain CVD 909. Infect. Immun. 68:4647-4652.

Wang, J. Y., M. F. Pasetti, F. Noriega, R. J. Anderson, S. S. Wasserman, J. E. Galen, M. Sztein, and M. M. Levine. 2001. Construction, genotypic and phenotypic characterization, and immunogenicity of attenuated DguaBA *Salmonella enterica* serovar Typhi strain CVD 915. Infect. Immun. 69:4734-4741.

Wu, K and T. K Wood. 1994. Evaluation of the hok/sok killer locus for enhanced plasmid stability. Biotechnol. Bioeng. 44:912-921.

What is claimed is:

1. A method for eliciting an immune response to a fusion protein in a subject comprising:
   administering to a subject a population of bacteria which produces and exports a fusion protein in an amount sufficient to elicit an immune response in said subject to said fusion protein, wherein said bacteria comprises an expression vector encoding said fusion protein, wherein said fusion protein comprises an export protein linked to a protein of interest in a 5' to 3' arrangement, wherein said export protein is Salmonella enterica serovar Typhi (S. Typhi) cytolysin A (ClyA) protein of SEQ ID NO: 2 or Escherichia coli hemolysin E (HlyE) protein encoded by the polynucleotide sequence set forth in SEQ ID NO:25, and wherein said bacteria is S. Typhi or *E. coli*;

thereby eliciting an immune response to said fusion protein in said subject.

2. The method of claim 1, wherein said bacteria is S. Typhi.

3. The method of claim 1, wherein said bacteria is *E. coli*.

4. The method of claim 1, wherein the export protein coding sequence is *Escherichia coli* hemolysin E (HlyE) protein encoded by the polynucleotide sequence set forth in SEQ ID NO: 25.

5. The method of claim 1, wherein the export protein coding sequence is the *Salmonella enterica* serovar Typhi (S. Typhi) cytolysin A (ClyA) protein of SEQ ID NO: 2.

6. A method for eliciting an immune response to a fusion protein in a subject comprising:

administering to a subject a population of bacteria which produces and exports a fusion protein in an amount sufficient to elicit an immune response in said subject to said fusion protein, wherein said bacteria comprises an expression vector encoding said fusion protein, wherein said fusion protein comprises an export protein linked to a protein of interest in a 5' to 3' arrangement, wherein export protein is *Salmonella enterica* serovar Typhi (S Typhi) cytolysin A (ClyA) protein of SEQ ID NO: 2 with one or more mutations resulting in amino acid substitutions selected from the group consisting of amino acid substitutions at positions 180, 185, 187, and 193, which attenuate the hemolytic activity of the export protein, and wherein said bacteria is S. Typhi *E. coli;* thereby eliciting an immune response to said fusion protein in said subject.

7. The method of claim 1, wherein the protein of interest is an antigen.

* * * * *